(12) United States Patent
Trygg et al.

(10) Patent No.: US 6,853,923 B2
(45) Date of Patent: Feb. 8, 2005

(54) ORTHOGONAL SIGNAL PROJECTION

(75) Inventors: Johan Trygg, Umeå (SE); Svante Wold, Vännäs (SE)

(73) Assignee: Umetrics AB, Umeå (SE)

( * ) Notice: Subject to any disclaimer, the term of this patent is extended or adjusted under 35 U.S.C. 154(b) by 309 days.

(21) Appl. No.: 10/204,646
(22) PCT Filed: Feb. 22, 2001
(86) PCT No.: PCT/SE01/00399
§ 371 (c)(1), (2), (4) Date: Aug. 19, 2002
(87) PCT Pub. No.: WO01/63441
PCT Pub. Date: Aug. 30, 2001

(65) Prior Publication Data
US 2003/0200040 A1 Oct. 23, 2003

(30) Foreign Application Priority Data
Feb. 22, 2000 (SE) .............................................. 0000563

(51) Int. Cl.$^7$ .............................................. G01N 31/00
(52) U.S. Cl. .............................. 702/23; 703/12; 436/8
(58) Field of Search ............................. 702/23, 19, 27, 702/30, 32, 86, 190; 703/12; 436/8, 43, 55

(56) References Cited

U.S. PATENT DOCUMENTS 5,379,238 A * 1/1995 Stark ............................ 703/11
6,480,795 B1 * 11/2002 Bossart et al. ............... 702/104
6,493,637 B1 * 12/2002 Steeg ............................ 702/19
6,593,572 B2 * 7/2003 Kelley .................... 250/339.05

FOREIGN PATENT DOCUMENTS

| EP | 0581023 | 2/1994 |
| WO | 9967722 | 12/1999 |

* cited by examiner

Primary Examiner—Marc S. Hoff
Assistant Examiner—Edward Raymond
(74) Attorney, Agent, or Firm—Ware, Fressola, Van Der Sluys & Adolphson LLP

(57) ABSTRACT

The invention provides a method and an arrangement for filtering or pre-processing most any type of multivariate data exemplified by NIR or NMR spectra measured on samples in order to remove systematic noise such as base-line variation and multiplicative scatter effects. This is accomplished by differentiating the spectra to first or second derivatives, by Multiplicative Signal Correction (MSC), or by similar filtering methods. The pre-processing may, however, also remove information from the spectra, as well as other multiple measurement arrays, regarding (Y) (the response variables). Provided is a variant of PLS that can be used to achieve a signal correction that is as close to orthogonal as possible to a given (y) vector or (Y) matrix. Hence, ensuring that the signal correction removes as little information as possible regarding (Y). A filter according to the present invention is named Orthogonal Partial Least Squares (OPLS).

20 Claims, 7 Drawing Sheets

ORTHOGONAL SIGNAL PROJECTION

BACKGROUND OF THE INVENTION

1. Field of Invention

The present invention pertains to a method for concentration or property calibration of substances or matter and an arrangement for calibration of spectroscopic input data from samples, whereby concentration or property calibration determines a model for further samples from the same type.

2. Description of Related Art

Multiple measurement vectors and arrays are increasingly being used for the characterization of solid, semi-solid, fluid and vapor samples. Examples of methods giving such multiple measurements are Near Infrared Spectroscopy (NIR) and Nuclear Magnetic Resonance (NMR) spectroscopy. Frequently the objective with this characterization is to determine the value of one or several concentrations in the samples. Multivariate calibration is then used to develop a quantitative relation between the digitized spectra, a matrix X, and the concentrations, in a matrix Y, as reviewed by H. Martens and T. Naes, Multivariate Calibration. Wiley, N.Y., 1989. NIR and other spectroscopies are also increasingly used to infer other properties Y of samples than concentrations, e.g., the strength and viscosity of polymers, the thickness of a tablet coating, and the octane number of gasoline.

The first step of a multivariate calibration is often to pre-process input data. The reason is that spectra, as well as other multiple measurement arrays, often contain systematic variation that is unrelated to the response y or the responses Y. For solid samples this systematic variation is due to, among others, light scattering and differences in spectroscopic path length, and may often constitute the major part of the variation of the sample spectra.

Another reason for systematic but unwanted variation in the sample spectra may be that the analyte of interest absorbs only in small parts of the spectral region. The variation in X that is unrelated to Y may disturb the multivariate modeling and cause imprecise predictions for new samples and also affect the robustness of the model over time.

For the removal of undesirable systematic variation in the data, two types of pre-processing methods are commonly reported in the analytical chemistry literature, differentiation and signal correction. Popular approaches of signal correction include Savitzky-Golay smoothing by A. Savitzky and M. J. E. Golay, Anal. Chem. 65, 3279–3289 (1993), multiple signal correction (MSC) H. Martens and T. Naes, Multivariate Calibration. Wiley, N.Y., 1989 and P. Geladi, D. MacDougall, and H. Martens, Linearization and Scatter-Correction for Near-Infrared Reflectance Spectra of Meat, Applied Spectroscopy, 3 (1985), 491–50, Fourier transformation by P. C. Williams and K. Norris, Near-Infrared Technology in Agricultural and Food Industries, American Cereal Association, St. Paul, Minn. (1987), principal components analysis (PCA) by J. Sun, Statistical Analysis of NIR data: Data pretreatment. J. Chemom. 11(1997) 525–532, variable selection H. Martens and T. Naes, Multivariate Calibration. Wiley, N.Y., 1989 and M. Baroni, S. Clementi, G. Cruciani, G. Constantino, and D. Riganelli. Predictive ability of regression models, Part 2: Selection of the best predictive PLS model. S. Chemom. 6 (1992) 347–56, and base line correction H. Martens and T. Naes, Multivariate Calibration. Wiley, N.Y., 1989 and R. J. Barnes, M. S. Dhanoa, and S. J. Lister. Standard Normal Variate Transformation and De-trending of Near-Infrared Diffuse Reflectance Spectra. Appl. Spectrosc. 43 (1989) 772–777.

These signal corrections are different cases of filtering, where a signal (e.g., a NIR spectrum) is made to have "better properties" by passing it through a filter. The objectives of filtering, often are rather vague; it is not always easy to specify what is meant by "better properties". Even, in the case of calibration, where it is possible to specify this objective in terms of lowered prediction errors or simpler calibration models, it is difficult to construct general filters that indeed improve these properties of the data.

Projections to latent structures by means of partial least squares (PLS) is one of the main generalized regression methods for analyzing multivariate data where a quantitative relationship between a descriptor matrix X and a quality matrix Y is wanted. Multivariate calibration, classification, discriminant analysis and pattern recognition are to name a few areas where PLS has shown to be a useful tool. The main reasons for its success are because it can cope with collinearity among variables, noise in both X and Y, moderate amounts of missing data in both X and Y, and it can also handle multiple Y simultaneously. These types of complicated data are now common due to the advent of analytical instruments such as HPLC, LC-UV, LC-MS, and spectroscopy instruments.

Improved and modified PLS methods using the so called NIPALS method, H. Wold, Nonlinear estimation by iterative least squares procedures in F David (Editor), Research Papers in Statistics, Wiley, N.Y., 1966 pp 411–444, have been suggested since the birth of PLS in 1977. A modification of the PLS method is presented. It aims at improving interpretation of PLS models, reduce model complexity, and improve predictions and robustness.

Spectroscopic methods represent a fairly cheap, quick and easy way of retrieving information about samples. In the characterization of organic substances such as wood, pulp, pharmaceutical tablets, ethanol content, etc., near infrared (NIR), NMR, and other instruments have proven useful.

SUMMARY OF THE INVENTION

The present invention sets forth a generic preprocessing method called orthogonal partial least squares (OPLS) for use in multivariate data analysis (MVA). The concept is to remove variation from X (descriptor variables) that is irrelevant to Y (quality variables, for example yield, cost or toxicity). In mathematical terms, this is equivalent as removing variation in X that is orthogonal to Y. Earlier, S. Wold, H. Antti, F. Lindgren, J. Öhman, Orthogonal signal correction of near-infrared spectra, Chemometrics and Intelligent Laboratory Systems, 44 (1998) 175–185, have described the orthogonal signal correction (OSC) technique, which has shown to be successful in removing information in X that is irrelevant to Y. In the present description, a method based on the same criteria, but with different means is disclosed.

According to the present invention the OPLS method improves the quality of a resulting calibration model regarding prediction ability, model parsimony, and interpretation.

In order to overcome problems and to achieve purposes, the present invention provides a method for concentration or property calibration of input data from samples of substances or matter, said calibration determining a filter model for further samples of the same substance or matter comprising to optionally transform, center, and scale the input data to provide a descriptor set and a concentration or property set. The method removes information or systematic variation in the input data that is not correlated to the concentration or property set by providing the steps of:

producing descriptor weight set, which is normalized, by projecting the descriptor set on the concentration or property set, projecting the descriptor set on the descriptor weight set, producing a descriptor score set, projecting the descriptor set on the descriptor score set, producing a descriptor loading set, projecting the property set on the descriptor score set, producing a property weight set, projecting the property set on the property weight set producing a property score set;

comparing the descriptor loading set and the descriptor weight set, and their difference, thus obtaining the part of the descriptor loading set that is unrelated to the property set;

using said difference weight set, normalized, as a starting set for partial least squares analysis;

calculating the corresponding orthogonal descriptor score set as the projection between the descriptor set and said normalized orthogonal difference weight set, and calculating a corresponding orthogonal descriptor loading set as the projection of the descriptor set onto the orthogonal descriptor score set;

removing the outer product of the orthogonal descriptor score set and the orthogonal descriptor loading set from the descriptor set, thus providing residuals data, which is provided as the descriptor set in a next component;

repeating the above steps for each orthogonal component;

the residuals data now being filtered from strong systematic variation that can be bilinearly modeled as the outer product of the orthogonal descriptor score set and the orthogonal descriptor loading set, thus providing an orthogonal descriptor set being orthogonal to the property set; and optionally providing a principal component analysis (PCA) on the orthogonal descriptor set, producing a bilinear decomposition of the orthogonal descriptor set as the outer product of the principal component analysis score set and the principal component analysis loading set and principal component analysis residuals, adding the principal component analysis residuals data back into filtered residuals data.

For filtering of new data, the method proceeds with the following two steps:

projecting a new descriptor set onto the normalized orthogonal difference weight set, thus producing a new orthogonal descriptor score set; and removing the product between the new orthogonal descriptor score set and the orthogonal descriptor loading set from the new descriptor set, thus providing new residuals, which are provided as a new descriptor set in a next orthogonal component.

The filtering steps for new data for all estimated orthogonal components are repeated as follows:

computing a new orthogonal descriptor set as the outer product of the new orthogonal descriptor score set and the orthogonal descriptor loading set, computing a new orthogonal principal component score set from the projection of the new orthogonal descriptor set onto the principal component analysis loading set, whereby the new principal component analysis models residuals formed are added back into the new residuals if principal component analysis was used on the orthogonal descriptor set, and only the outer product of the principal component analysis score sets and the principal components loading set was removed from the original descriptor set.

For multiple concentration or property sets, a principal component analysis model is calculated on said property sets and the above steps are repeated for each separate principal component analysis score set using the orthogonal descriptor as the input descriptor set for each subsequent principal component analysis score set, thus making up a filtering method for filtering of further samples of the same type.

Further, performing an ordinary PLS analysis with the filtered residuals data and the concentration or property set, and an ordinary PLS analysis with said filtered new residuals set as prediction set.

In one embodiment of the present invention, by finding said orthogonal components for each component separately, an amount of disturbing variation in each partial least square component can be analyzed.

Another embodiment uses crossvalidation and/or eigenvalue criteria for reducing overfitting.

In a further embodiment, principal component analysis (PCA) components are chosen according to a crossvalidation or eigenvalue criteria.

In a still further embodiment, specific types of variation in the descriptor set are removed, when an unwanted or non-relevant concentration or property set exist by using the orthogonal descriptor as a data set of interest, as it contains no correlated variation to the concentration or property set.

The present invention also sets forth an arrangement for concentration or property calibration of input data from samples of substances or matter, said calibration determining a filter model for further samples of the same substance or matter comprising to optionally transform, center, and scale the input data to provide a descriptor set and a concentration or property set.

The filter model removes information or systematic variation in the input data that is not correlated to the concentration or property set and comprises:

projecting means for producing a descriptor weight set, which is normalized, by projecting the descriptor set on the concentration or property set;

projecting means for the descriptor set on the descriptor weight set producing a descriptor score set;

projecting for the descriptor set on the descriptor score set producing a descriptor loading set;

projecting means for the property set on the descriptor score set producing a property weight;

projecting means for the property set on the property weight set producing a property score set;

comparing means for the descriptor loading set and the descriptor weight set, and their difference, thus obtaining the part of the descriptor loading set that is unrelated to the property set;

using said difference weight set, normalized, as a starting set for partial least squares analysis;

first calculating means for the corresponding orthogonal descriptor score set as the projection between the descriptor set and said normalized orthogonal difference weight set, and for calculating a corresponding orthogonal descriptor loading set as the projection of the descriptor set onto the orthogonal descriptor score set; and second calculating means for removing the outer product of the orthogonal descriptor score set and the orthogonal descriptor loading set from the descriptor set, thus providing residuals data, which is provided as the descriptor set in a next component.

The filtering model uses the above means and steps for each orthogonal component, and further comprises:

first filtering means for the residuals data from strong systematic variation that can be bilinearly modeled as the outer product of the orthogonal descriptor score set and the orthogonal descriptor loading set, thus providing an orthogonal descriptor set being orthogonal to the property set;

The filtering means may also optionally include analyzing means for a principal component analysis (PCA) on the orthogonal descriptor set, producing a bilinear decomposition of the orthogonal descriptor set as the outer product of the principal component analysis score set and the principal component analysis loading set and principal component analysis residuals, adding the principal component analysis residuals data back into filtered residuals data.

The invention may also include second filtering means for filtering a new data for all estimated orthogonal componenets, including the following means;

projecting means for a new descriptor set onto the normalized orthogonal difference weight set, thus producing a new orthogonal descriptor score set; and calculating means for removing the product between the new orthogonal descriptor score set and the orthogonal descriptor loading set from the new descriptor set, thus providing new residuals, which are provided as a new descriptor set in a next orthogonal component.

The filtering model uses said filtering of new data for all estimated orthogonal components, and further comprises:

computing means for a new orthogonal descriptor as the outer product of the new orthogonal descriptor score set and the orthogonal descriptor loading set, computing a new orthogonal principal component score set from the projection of the new orthogonal descriptor set onto the principal component analysis loading set, whereby the new principal component analysis residuals are added back into the new residuals (enew') if principal component analysis was used on the orthogonal descriptor set, and only removing the outer product of the principal component analysis score sets and the principal components loading set from the original descriptor set.

For multiple concentration or property sets, calculating a principal component analysis model on said property sets and repeatedly using the above means for each separate principal component analysis score set and using the orthogonal descriptor as the input descriptor set for each subsequent principal component analysis score set, thus making up a filtering method for filtering of further samples of the same type.

The arrangement further comprising partial least square analysis means for the filtered residuals data and the concentration or property set, and for said filtered new residuals set as prediction set.

The arrangement further being capable of performing other embodiments of the method in accordance with the attached dependent claims.

BRIEF DESCRIPTION OF THE DRAWING

For a more complete understanding of the present invention and for further objectives and advantages thereof, reference may now be had to the following description taken in conjunction with the accompanying drawings, in which:

FIG. 2a illustrates column centered untreated NIR spectra, and a lower FIG. 2b shows OPLS treated NIR spectra in accordance with the present invention;

DETAILED DESCRIPTION OF THE INVENTION

Figure 1:
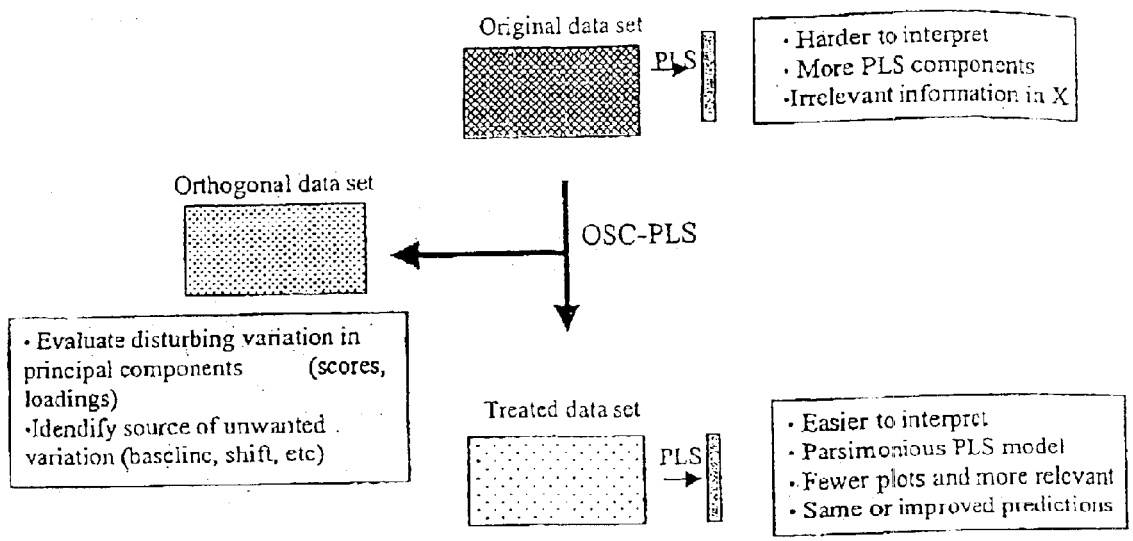
FIG. 1 illustrates an overview of orthogonal partial least squares (OPLS) in accordance with the present invention.

The present invention provides a method and apparatus to remove systematic information from an input data set X irrelevant for the concentration or property set y or Y. In other words, to remove variability in X that is orthogonal to Y. A pre-processing method with a similar concept as orthogonal signal correction OSC is disclosed through the present invention, named orthogonal partial least squares (OPLS).

The following are definitions:

A vector, matrix and the like are defined as being sets, for example, a set may be a vector, a matrix or the like.

Primed vectors or matrixes are mathematically transposed.

A component in PCA or PLS represents a new latent variable produced from summarizing old variables by means of projection.

A loading set describes the orientation of an obtained component in relation to original variables in a data matrix X.

The character y defines a column vector and Y depicts a matrix, i.e., several column vectors.

The proposed OPLS according to the present invention analyzes disturbing variation in each PLS component. The disturbing variation in X is separated from relevant variation, improving interpretation and analysis of filtered input data X, and with the additional bonus that irrelevant variation itself can be studied and analyzed.

In an example given using near infrared reflectance (NIR) spectra on wood chips, applying OPLS as preprocessing method, resulted in reduced PLS model complexity with preserved prediction ability, effective removal of disturbing variation in data, and not at least, improved interpretational ability of both wanted and unwanted variation in data.

Removing irrelevant variation in data prior to data modeling is interesting not only from a predictive point of view, the interpretational ability of resulting models also improves.

Interpretation of all provided models is very important. From interpretation more information and knowledge of a system can be retrieved and analyzed, and developed further.

Multiplicative scatter correction (MSC) is a method developed by Geladi et al. The method was developed to assist in circumventing problems found in spectrum from near infrared reflectance spectroscopy in multivariate calibration. Additive and multiplicative scatter effects produce variations in a NIR spectrum that are difficult to cope with in calibration models. The MSC method calculates parameters a and b through regression of each of the spectra onto a target spectrum, usually the mean spectrum, $x_m$. $X_i=a_i-x_m b_i$. Parameters a,b are further used to update the NIR spectrum using the following formula:

MSC correction filter $X_{i\ corr}=(X_i-a_i)/b_i$

A major problem with MSC is that the parameters a, b are determined regardless of Y. In multivariate calibration, this means that MSC can actually remove variation in X that is relevant for the modeling of y or Y, thereby producing worse calibration models and increase prediction residuals. The standard normal variate transform (SNV) developed by Barnes is similar to MSC. Here, the updating parameters a and b are calculated from each spectrum individually, $a_i$ represents the mean of spectrum $X_i$, and $b_i$ is the standard deviation of row $X_i$. SNV is analogous to unit variance (UV) scaling and centering each row.

SNV: $X_i = (X_i - a_i)/b_i$.

$a_i$ = mean of row $i$, $b_i = \sqrt{\dfrac{\sum(X_i - a_i)^2}{d.f.}}$ on row $i$.

The SNV parameters are also determined regardless of Y, which could result in worse calibration models and higher prediction residuals.

Andersson recently reported another preprocessing method called direct orthogonalization (DO), C. A. Andersson, "Direct orthogonalization, Chemometrics and Intelligent laboratory systems", 47 (1999) 51–63. It also attempts to remove variation in X that is orthogonal to Y. Unfortunately, this method fails because it does not, contrary to what the name implies, guarantee orthogonal information being removed. Therefore DO can not be classified as an orthogonal filtering method.

The steps in the direct orthogonalization method are shown below:
1.) X and Y are centered,
2.) w=X'y(y'y)$^{-1}$, project X on Y,
3.) X_ortho=X−Yw', Orthogonalize X to Y,
4.) X_ortho=T_orthoP'_ortho+E , Decompose X_ortho into principal components, keep loadings P,
5.) T=XP_ortho, Calculate new scores T from original X and orthogonal loadings P,
6.) $X_{do}$=X−TP'_ortho,
7.) Calculate calibration model using $X_{do}$ and Y,
8.) For new column centered samples, $T_{pred}=X_{pred}$P_ortho, and
9.) $X_{do\_pred}=X_{pred}-T_{pred}$P'_ortho.

There are some major problems with the suggested approach. The crucial one being step 5. Instead of using the orthogonal scores T_ortho from step 4, Andersson calculates a new set of scores T with the loadings P_ortho from the original X matrix. These new T scores are not orthogonal to Y, which means that variation in data relevant for the modeling of Y can be removed in step 6, resulting in worse calibration models and higher prediction errors. The same situation occurs for new unknown samples to be predicted in step 8. If the method had used the orthogonal scores calculated in step 4, the variation removed from X would have been orthogonal. However, the problem would then be the updating of new samples because no Y exists for them. This problem was earlier mentioned by Wold.

The orthogonal signal correction (OSC) method introduced by Wold et al, represented a new exciting concept in multivatiate data analysis and modeling. The idea behind it is to remove information in X that is irrelevant for the modeling of Y. This is accomplished by removing information or variability in X that is non-correlated or orthogonal to Y.

There are three criteria put on the OSC solution:
Should involve large systematic variance in X,
Must be predictive by X (in order to apply on future data), and
Removed information from X must be orthogonal to Y.

The first two criteria are easily met. A regular PCA solution provides that. However, the third and most important criteria is not easily met. It requires a time-consuming iteration to find an OSC solution that satisfies all three criteria simultaneously.

A solution often converges quickly, but it still needs 10–20 iterations. The OSC solution is not unique but depends on a starting vector t. Therefore, PCA is a good choice to produce the starting vector because it gives the longest t vector, that can be predicted by X. Two of the criteria above are then automatically met. During an OSC iteration, the length of the t vector will decrease some in order to converge the OSC solution.

---

An outline of the OSC solution is as follows:

(1) Optionally transform, center and scale the data to give the 'raw' matrices X and Y.
(2) Start by calculating the first principal component of X, with the score vector, t.
(3) Orthogonalize t to Y,   $t_{new} = (I - Y(Y'Y)^{-1}Y')t$.
(4) Calculate a normalized weight vector, w, that makes Xw = $t_{new}$. This is done by a -continued An outline of the OSC solution is as follows:

PLS estimation giving a generalized inverse = $X^-w = X^-t_{new}$.
(5) Calculate a new score vector from X and w    t = Xw.
(6) Check for convergence, by testing if t has stabilized. Convergence if norm(t − $t_{new}$)/ norm(t) < $10^{-6}$, if not convergence, return to step 3, otherwise, continue to step 7.
(7) Compute a loading vector, p (needed for orthogonality between components)
$$p' = t'X/(t't).$$
(8) Subtract the 'correction' from X, to give residuals, E.
(9) Continue with the next 'component' using E as X, then another, etc., until satisfaction.
(10) New samples (the prediction set) are corrected using W and P of the calibration model. For each new observation vector, $x_{new}$:
$$t1 = x_{new}w_1$$
$$e_1 = x_{new} - t_1p_1,$$
$$t2 = e_1w_2,$$
$$e_2 = e_1 - t_2p_2' \text{ and so on.}$$

The main problem with OSC has been concerned with the overfitting of the orthogonal components. Crossvalidation or any other validation method is not used in OSC, the additional time needed for this has been one of the obstacles. The correct number of "internal PLS components" to estimate the orthogonal components are therefore difficult to estimate, leading to overfitting and sometimes degradation of resulting calibration models. The OSC method is quite computer intensive for larger data sets (K>2000), due to the iteration to estimate the orthogonal components.

The orthogonal partial least squares (OPLS) method according to the present invention has a like criteria as OSC, namely to remove variation in X irrelevant to y or Y.

Outline of the OPLS method for single properties
Optionally transform, center and scale the data to give the 'raw' matrices X and y

| | | |
|---|---|---|
| 1. | $w' = y'X/y'y$ | Project X on y |
| 2. | $w = w/\|w\|$ | Normalize w |
| 3. | $t = Xw/(w'w)$ | Project X on w |
| 4. | $c' = t'y/(t't)$ | Project y on t |
| 5. | $u = yc/(c'c)$ | Project y on c |
| 6. | $p' = t'X/(t't)$ | Project X on t |
| 7. | $w_{ortho} = p - w'p/(w'w)w$ | Find orthogonal loading in p |
| 8. | $w_{ortho} = w_{ortho}/\|w_{ortho}\|$ | Normalize orthogonal loading $w_{ortho}$ |
| 9. | $t_{ortho} = X\ w_{ortho}/(w_{ortho}'w_{ortho})$ | Project X on $w_{ortho}$ |
| 10. | $p_{ortho}' = t_{ortho}'X/(t_{ortho}'t_{ortho})$ | Project X on $t_{ortho}$ |
| 11. | $E_{opls} = X - t_{ortha}\ P_{ortho}'$ | Remove orthogonal variation from X |
| 12. | $T_{ortho} = [T_{ortho}t_{ortho}],$ $P_{ortho} = [P_{ortho}p_{ortho}],$ $w_{ortho} = [W_{ortho}W_{ortho}];$ | Save found parameters. Return to step 1 and set X = $E_{opls}$ for additional orthogonal components, otherwise continue to step 13. |
| 13. | $X_{ortho} = T_{ortho}*P_{ortho}$ | Orthogonal variation in X. Analyze variation component wise, or run PCA on $X_{ortho}$ (step 14). |
| 14. | $X_{ortho} = T_{pca\_ortho}*P_{pca\_ortho}' + E_{pca\_ortho}$ | Principal component analysis (PCA) on $X_{ortho}$ to summarize latent orthogonal variation Removing all estimated orthogonal variation from X is one option. Another option is to only remove the latent orthogonal components estimated from the PCA in step 14. This corresponds to adding $E_{pca\_ortho}$ back into $E_{opls}$. |
| 15. | New or future samples (the prediction set) are corrected using $W_{ortho}$ and $P_{ortho}$ of the calibration model. For each new observation vector $x_{new}'$ repeat steps 16–18 for each orthogonal component estimated in the calibration model. | |
| 16. | $t_{new\_ortho} = x_{new}'\ w_{ortho}/(w_{ortho}'w_{ortho})$ | Calculate orthogonal score in $x_{new}'$ |
| 17. | $t_{new\_ortho} = [t_{new\_ortho}t_{new\_ortho}]$ | Save orthogonal scores for prediction set |
| 18. | $e_{new\_opls}' = x_{new}' - t_{new\_ortho}\ P_{ortho}'$ | Orthogonal component in $x_{new}'$ is removed. Set $x_{new}' = e_{new\_opls}'$. Proceed to step 19 when all orthogonal components have been estimated. |
| 19. | $x_{new\_ortho} = t_{new\_ortho}*P_{ortho}'$ | Orthogonal variation in $x_{new}'$ |
| 20. | $t_{new\_pca\_ortho} = x_{new\_ortho}P_{pca\_ortho}$ | Estimate new scores from PCA in step 14 |
| 21. | $x_{new\_ortho} = t_{new\_pca\_ortho}P_{pca\_ortho}' + e_{new\_pca\_ortho}$ | If only the orthogonal latent components from PCA on $X_{ortho}$ was removed then $e_{new\_pca\_ortho}$ should be added back to $e_{new\_opls}$. |

An outline of the OPLS method for multiple properties is as follows:

An outline of the OPLS method shown here for a matrix Y with multiple properties. An example of multiple properties could be temperature and moist content or any other relevant multiple property.

Optionally transform, center and scale the raw data to give the matrices X and Y 1. $w' = y'X/(y'y)$         For each column in Y estimate the corresponding w, and create a matrix $W = [W \ w]$.
2. $W = T_w P_w' + E_w$     Estimate with principal component analysis (PCA), the principal components of W as long as the ratio of the sum of squares of the current score vector $t_w$ divided by the sum of squares of W is larger than a given threshold, typically $10^{-10}$.
3. Estimate a regular multi-Y PLS component with given X and Y. (steps 4–9)
4. Initialize multi-Y PLS calculation by setting a column in Y to u.
5. $w' = u'X/(u'u)$       Repeat steps 5–9 until convergence.
6. $w = w/\|w\|$
7. $t = Xw/(w'w)$
8. $c' = t'Y/(t't)$
9. $u = Yc/(c'c)$          Check convergence, if $\|u_{new} - u_{old}\|/\|u_{new}\| < 10^{-10}$ continue to step 10, otherwise return to step 5.
10. $p' = t'X/(t't)$        To estimate an orthogonal component, go to step 11, otherwise go to step 17.
11. $p = (p - ((t_w'p)/(t_w't_w))t_w$     Orthogonalize p to each column in $T_w$, then set $w_{ortho} = p$. In this way orthogonality to all Y variables are ensured for resulting orthogonal score vector in step 13. p vector in this step can also be an arbitrary vector (e.g. PCA loading of X).
12. $w_{ortho} = w_{ortho}/\|w_{ortho}\|$
13. $t_{ortho} = Xw_{ortho}/(w_{ortho}'w_{ortho})$
14. $p_{ortho}' = t_{ortho}'X/(t_{ortho}'t_{ortho})$
15. $E_{O-PLS} = X - t_{ortha} p_{ortho}'$     $E_{O-PLS}$ are the filtered data.
16. Save found parameters $T_{ortho} = [T_{ortho} \ t_{ortho}]$, $P_{ortho} = [P_{ortho} \ p_{ortho}]$, $W_{ortho} \ w_{ortho}]$. Return to step 4 and set $X = E_{O-PLS}$.
17. To find orthogonal variation for the next PLS component, remove current PLS component from X and Y and save the parameters for this PLS component for future samples $E = X - tp'$, $F = Y - tc'$, $T_{pls} = [T_{pls} t]$, $W_{pls} = [W_{pls} \ w]$, $P_{pls} = [P_{pls} p]$ and return to step 1 and set $X = E$ and $Y = F$, otherwise to stop, go to step 18.
18. $X_{ortho} = T_{ortho} P_{ortho}'$ Analyze orthogonal variation component wise, or run PCA on $X_{ortho}$ (step 19).
19. $X_{ortho} = T_{pca\_ortho} P_{pca\_ortho}' + E_{pca\_ortho}$ Principal component analysis (PCA) of $X_{ortho}$ to summarize the systematic orthogonal variation. Removing all estimated orthogonal variation from X is one option, another option is to only remove the principal orthogonal components estimated in step 19. This corresponds to adding $E_{pca\_ortho}$ back into $E_{O-PLS}$.
20. $E_{O-PLS} = E_{O-PLS} + T_{pls} P_{pls}'$     Add the PLS components removed back into $E_{O-PLS}$ which now contains the filtered data.
21. New or future samples (the prediction set) are corrected using $W_{ortho}$, $P_{ortho}$, $W_{pls}$ and $P_{pls}$ from the calibration model. For each new observation vector $x_{new}'$, repeat steps 22–26 for each component (O-Pbs or PLS) in the order they were calculated in the calibration model.
22. If component = OPLS: $t_{new\_ortho} = x_{new} W_{ortho}/(W_{ortho}'W_{ortho})$
23. If component = OPLS: $t_{new\_ortho}' = [t_{new\_ortho}' t_{new\_ortho}]$ Save orthogonal scores for prediction set. The first t in the brackets is a vector while the second t is a scalar.
24. If component = OPLS: $e_{new\_O-PLS}' = x_{new}' - t_{new\_ortho} P_{ortho}'$     Orthogonal component in $x_{new}'$ is removed. Set $x_{new}' = e_{new\_O-PLS}'$ for additional components and return to step 21, otherwise proceed to step 27.
25. if component = PLS: $t_{new\_pls} = x_{new} W_{pls}/(W_{pls}'W_{pls})$, $t_{new\_pls}' = [t_{new\_pls}' t_{new\_pls}]$. The first in the brackets is a vector while the second t is a scalar.
26. if component = PLS: $e_{new\_pls}' = x_{new}' - t_{new\_pls} P_{pls}'$ PLS component in $x_{new}'$ is removed. Set $x_{new}' = e_{new\_pls}'$ and return to step 22.
27. $x_{new\_ortho}' = t_{new\_ortho} P_{ortho}'$
28. $t_{new\_pca\_ortho}' = x_{new\_ortho}' P_{pca\_ortho}$     Estimate new scores from PCA loadings in step 19 $x_{new\_ortho}' = t_{new\_pca\_ortho}' P_{pca\_ortho}' + e_{new\_pca\_ortho}'$ If only the orthogonal latent components from PCA on $X_{ortho}$ was removed then $e_{new\_pca\_ortho}'$ should be added back to $e_{new\_O-PLS}'$.
29. $e_{new\_O-PLS}' = e_{new\_O-PLS}' + t_{new\_pls} P_{pls}'$ Add the PLS components back into $e_{new\_O-PLS}'$ which contains the filtered data.

For multiple Y, run principal component analysis (PCA) on Y and repeat the method above for each separate Y score. Use $X_{ortho}$ as the input X matrix after the first round. Then orthogonality for all Y variables are guaranteed.

In the area of semi-empirical modeling, the obvious advantages with OPLS are more parsimonious PLS model (fewer components), and improved interpretation because the disturbing variation, and the relevant variation have been separated. OPLS should give an improved detection limit for moderate outliers in the scores because irrelevant variations in X could have different statistical distributions than the relevant variation, producing a disturbance to the calculation of for example the Hotelling's $T^2$ statistic.

Another advantage with OPLS compared to earlier proposed OSC method is that no time-consuming internal iteration is present, making it very fast to calculate. Also, the risk of overfitting is greatly reduced with OPLS, because crossvalidation and/or some eigenvalue criteria is used, resulting in systematic and relevant components being calculated and extracted. OPLS is a modification of the original PLS NIPALS method for effectively separating relevant and irrelevant variation in order to improve the interpretation of data. The number of orthogonal components should be selected according to a significance criteria. Used herein is a combination of looking at how much orthogonal variation is removed for each component, and the normalized difference between p and $w_{ortho}$. A regular crossvalidation with Y is not possible because the c weight parameter is always zero for all orthogonal components.

FIG. 1 provides an overview of the OPLS method according to the present invention. The overview is commented in blocks of text in FIG. 1 where the advantages and disadvantages regarding OPLS pretreated PLS models versus PLS models without pretreatment are stated. A regular PLS model, thus is harder to interpret, more components are needed and X contains irrelevant information. The OPLS pretreated PLS model, thus has the advantages of being easier to interpret, the resulting PLS model is more parsimonious, plots of parameters such as scores and loadings are more relevant and predictions can be improved.

Principal component analysis (PCA) can be used to decompose the already orthogonal matrix X_ortho into orthogonal principal components. The number of PCA components can be chosen according to some significance criteria, i.e. crossvalidation or eigenvalue. Analyzing the irrelevant variation is most valuable, the source of disturbing variation can perhaps be identified and removed, or at least understood where it comes from.

It is important to realize that all variation in the scores and loading plots are disturbances and can be interpreted without regarding the influence on Y. The information from such analysis is very important, not at least for industrial process data which contain large unknown variations due to fluctuating process environments that are hard to remove, but awareness of what they are could be vital for further process improvements. Also, instead of removing the orthogonal PLS components from the original data, another suggested approach that works well is to run PCA on the orthogonal data matrix, and only remove the principal components from the orthogonal data matrix. The residual left is inserted into the OPLS treated X matrix. This has shown to improve the predictions, and to decrease the total number of components used drastically. The results of such analysis are shown in attached Table 1.

According to the present invention there also exists another useful method to estimate and remove irrelevant variation from X with respect to a given Y, and that method converges with the OPLS solution if PCA is used on the orthogonal data matrix $X_{ortho}$ as suggested in OPLS method. This method is herein named projected orthogonal signal correction, POSC. It requires an initial fully estimated PLS model to be calculated, and it can not extract an orthogonal PLS component for each PLS component as OPLS is able to.

The method of the present invention can thus be summarized as a method for concentration or property calibration of input data from samples of substances or matter, said calibration determining a filter model for further samples of the same substance or matter comprising to optionally transform, center, and scale the input data to provide a descriptor set X and a concentration or property set y, Y. It removes information or systematic variation in the input data that is not correlated to the concentration or property set by providing the steps of:

producing a descriptor weight set w, which is normalized, by projecting the descriptor set X on the concentration or property set y, Y, projecting the descriptor set X on the descriptor weight set w producing a descriptor score set t, projecting the descriptor set X on the descriptor score set t producing a descriptor loading set p, projecting the property set y on the descriptor score set t producing a property weight set c, projecting the property set y on the property weight set c producing a property score set u;

comparing the descriptor loading set p and the descriptor weight set w, and their difference p−w, thus obtaining the part of the descriptor loading set p that is unrelated to the property set y;

using said difference weight set which, normalized, as a starting set for partial least squares analysis;

calculating the corresponding orthogonal descriptor score set tortho as the projection between the descriptor set X and said normalized orthogonal difference weight set wortho, and calculating a corresponding orthogonal descriptor loading set portho as the projection of the descriptor set X onto the orthogonal descriptor score set tortho;

removing the outer product of the orthogonal descriptor score set tortho and the orthogonal descriptor loading set portho' from the descriptor set X, thus providing residuals data E, which is provided as the descriptor set X in a next component;

repeating the above steps for each orthogonal component;

the residuals data E now being filtered from strong systematic variation that can be bilinearly modeled as the outer product of the orthogonal descriptor score set and the orthogonal descriptor loading set Tortho*Portho', thus providing an orthogonal descriptor set Xortho being orthogonal to the property set y, Y.

Optionally a principal component analysis (PCA) can be provided on the orthogonal descriptor set Xortho, producing a bilinear decomposition of the orthogonal descriptor set Xortho as the outer product of the principal component analysis score set and the principal component analysis loading set and principal component analysis residuals Tpcaortho*Ppcaortho'+Epcaortho. Whereby the principal component analysis residuals data Epcaortho can be added back into filtered residuals data E.

For filtering new data, the following steps are provided:

projecting a new descriptor set xnew' onto the normalized orthogonal difference weight set wortho, thus producing a new orthogonal descriptor score set tnewortho; and removing the product between the new orthogonal descriptor score set tnewortho and the orthogonal descriptor loading set portho' from the new descriptor set xnew', thus providing new residuals enew', which are provided as a new descriptor set xnew' in a next orthogonal component.

The filtering steps being repeated for new data for all estimated orthogonal components; including computing a new orthogonal descriptor set xnewortho'=tnewortho*Portho' as the outer product of the new orthogonal descriptor score set tnewortho and the orthogonal descriptor loading set portho', computing a new orthogonal principal component score set tnewpcaortho from the projection of the new orthogonal descriptor set onto the principal component analysis loading set xnewortho'*Ppcaortho'. Whereby the new principal component analysis residuals formed enewpcaortho=xnewortho'−tnewpcaortho* Ppcaortho' are added back into the new residuals enew' if principal component analysis was used on the orthogonal descriptor set Xortho, and only the outer product of the principal component analysis score sets and the principal components loading set Tpcaortho*Ppcaortho' was removed from the original descriptor set X.

For multiple concentration or property sets Y, calculating a principal component analysis model on said property sets Y=TP'+E and repeating the above steps for each separate principal component analysis score set t and use the orthogonal descriptor $X_{ortho}$ as the input descriptor set X for each subsequent principal component analysis score set t, thus making up a filtering method for filtering of further samples of the same type.

Proceeding with performing an ordinary PLS analysis with the filtered residuals data E and the concentration or property set y, Y, and with said filtered new residuals set enew' as the prediction set.

The present invention also sets forth an arrangement for concentration or property calibration of input data from samples of substances or matter.

A filter model comprised in the arrangement removes information or systematic variation in the input data that is not correlated to the concentration or property set and comprises:

projecting means for producing a descriptor weight set w, which is normalized, by projecting the descriptor set X on the concentration or property set y, Y;

projecting means for the descriptor set X on the descriptor weight set w producing a descriptor score set t;

projecting means for the descriptor set X on the descriptor score set t producing a descriptor loading set p;

projecting means for the property set y on the descriptor score set t producing a property weight set c;

projecting means for the property set y on the property weight set c producing a property score set u;

comparing means for the descriptor loading set p and the descriptor weight set w, and their difference p−w, thus obtaining the part of the descriptor loading set p that is unrelated to the property set y, Y;

using said difference weight set wortho, normalized, as a starting set for partial least squares analysis;

first calculating means for the corresponding orthogonal descriptor score set tortho as the projection between the descriptor set X and said normalized orthogonal difference weight set wortho, and for calculating a corresponding orthogonal descriptor loading set portho as the projection of the descriptor set X onto the orthogonal descriptor score set tortho; and second calculating means for removing the outer product of the orthogonal descriptor score set tortho and the orthogonal descriptor loading set portho' from the descriptor set X, thus providing residuals data E, which is provided as the descriptor set X in a next component.

The filtering model uses the above means and steps for each orthogonal component; and further comprises:

first filtering means for the residuals data E from strong systematic variation that can be bilinearly modeled as the outer product of the orthogonal descriptor score set and the orthogonal descriptor loading set Tortho*Portho', thus providing an orthogonal descriptor set Xortho being orthogonal to the property set y, Y;

The arrangement is optionally providing analyzing means for a principal component analysis (PCA) on the orthogonal descriptor set Xortho, producing a bilinear decomposition of the orthogonal descriptor set Xortho as the outer product of the principal component analysis score set and the principal component analysis loading set and principal component analysis residuals Tpcaortho*Ppcaortho'+Epcaortho, adding the principal component analysis residuals data Epcaortho back into filtered residuals data E.

Second filtering means for new data includes the following means:

projecting means for a new descriptor set xnew' onto the normalized orthogonal difference weight set wortho, thus producing a new orthogonal descriptor score set tnewortho; and calculating means for removing the product between the new orthogonal descriptor score set tnewortho and the orthogonal descriptor loading set portho' from the new descriptor set xnew', thus providing new residuals enew', which are provided as a new descriptor set xnew' in a next orthogonal component;

The filtering step being repeated for new data for all estimated orthogonal components with the filtering means comprising:

computing means for a new orthogonal descriptor set xnewortho'=tnewortho*Portho' as the outer product of the new orthogonal descriptor score set tnewortho and the orthogonal descriptor loading set portho', computing a new orthogonal principal component score set tnewpcaortho from the projection of the new orthogonal descriptor set onto the principal component analysis loading set xnewortho'*Ppcaortho'. Whereby the new principal component analysis residuals formed enewpcaortho=xnewortho'−tnewpcaortho* Ppcaortho' are added back into the new residuals (enew') if principal component analysis was used on the orthogonal descriptor set Xortho, and only removing the outer product of the principal component analysis score sets and the principal components loading set Tpcaortho*Ppcaortho' from the original descriptor set X.

For multiple concentration or property sets Y, calculating a principal component analysis model on said property sets Y=TP'+E and repeatedly using the above means and steps for each separate principal component analysis score set t and using the orthogonal descriptor $X_{ortho}$ as the input descriptor set X for each subsequent principal component analysis score set t, thus making up a filtering method for filtering of further samples of the same type.

Applying partial least square analysis means for the filtered residuals data E and the concentration or property set y, Y, and for said filtered new residuals set enew' as a prediction set.

It is to be understood that the means making up the arrangement can be purely software means, hardware means known in the art or combinations of them.

| The following is an outline of the POSC method for a single property: | | |
|---|---|---|
| 1.) | Optionally transform, center and scale the data to give the 'raw' matrices X and y | |
| 2.) | t = X*w | Calculate normalized loading w from some regression method to estimate t representing the best systematic correlation to Y. |
| 3.) | p' = t'X/(t't) | Project X on t to get loading p. |
| 4.) | X_ortho = X − tp' | |
| 5.) | X_ortho = T_orthoP_ortho' + E_ortho | Calculate a regular PCA model with xx number of chosen components |
| 6.) | Xposc = X − T_orthoP_ortho' | Filtered data Xposc |

-continued

The following is an outline of the POSC method for a single property:

7.) New or future data (the prediction set) are corrected using w,p and P_ortho from the calibration model. For each new observation vector x_test' repeat steps 11–14 for each orthogonal component estimated in the calibration model
8.) t_test = x_test'w            Calculate score in x_test'
9.) x_test_ortho' = x_test' − t_test p'    Orthogonal variation in new data
10.) Repeat steps 11 and 14 for each orthogonal component removed in step 5
11.) t_test_ortho = x_test_ortho'p_ortho
12.) t_test_ortho = [t_test_ortho t_test_ortho] Save orthogonal scores for prediction set
13.) e_test_ortho' = x_test_ortho' − t_test_ortho p_ortho'
14.) For each remaining orthogonal component, set x_test_ortho' = e_test_ortho' and return to step 11, else proceed to step 15
15.) xposc_test' = x_test' − t_test_orthoP_ortho'      Filtered new data xposc_test'

The following is an outline of the POSC method for multiple properties:

The outline of the proposed POSC method shown here for the matrices X and Y where Y has multiple properties. An example of multiple properties could be temperature and moist content or any other relevant multiple property.

The OPLS model and the original PLS model will give similar results regarding explained variance in Y unless the OPLS treated X matrix is scaled prior to PLS modeling. Improvements in prediction in the resulting OPLS model compared to the original PLS model can occur if the OPLS treated data matrix X is scaled prior to PLS modeling.

Optionally transform, center avid scale the raw data to give the matrices X and Y, as follows:

1. $T = XW$      Calculate the normalized regression coefficients W from some regression method (e.g. PLS) to estimate T, representing the best systematic correlation to Y.
2. $T = T_{pca}P_{pca}' + E_{pca}$    Estimate with principal component analysis (PCA), the principal components of T as long as the ratio of the sum of squares of the current score vector $t_{pca}$ divided by the sum of squares of T is larger than a given threshold, typically $10^{-10}$.
3. $p' = t_{pca}'X/(t_{pca}'t_{pca})$    Estimate p for each column in $T_{pca}$, resulting in matrix P
4. $X_{ortho} = X − T_{pca}P'$
5. $X_{ortho} = T_{ortho}P_{ortho}' + E_{ortho}$    Calculate a PCA model
6. $X_{posc} = X − T_{ortho}P_{ortho}'$    Remove the systematically irrelevant variation
7. New or future data (the prediction set) are corrected using W, $P_{pca}$, P and $P_{ortho}$ from the calibration model. For each new observation vector $x_{test}'$ repeat steps 10–13 for each orthogonal component estimated in the calibration model
8. $t_{test}' = x_{test}'W$
9. $t_{testpca}' = t_{test}'P_{pca}$
10. $x_{test\_ortho}' = x_{test}' − t_{testpca}'P'$    Orthogonal variation in new data
11. Repeat steps 12–14 for each orthogonal principal component removed in step 6
12. $t_{test\_ortho} = x_{test\_ortho}'p_{ortho}$
13. $t_{test\_ortho}' = [t_{test\_ortho} t_{test\_ortho}]$    Save $t_{test\_ortho}$, the first t in the brackets is a vector while the second t is a scalar.
14. $e_{test\_ortho}' = x_{test\_ortho}' − t_{test\_ortho}'p_{ortho}'$    For each remaining orthogonal component, set $x_{test\_ortho}' = e_{test\_ortho}'$ and return to step 12 to remove any additional orthogonal component earlier estimated, else proceed to step 15.
15. $x_{posc\_test}' = x_{test}' − t_{test\_ortho}'P_{ortho}'$    Filtered new data $x_{posc\_test}'$.

All projection methods working after some least squares methodology are sensitive to abnormal occurrences in data. PLS and PCA are no different. It is important to realize that detection and investigation of abnormal data or outliers represent an important part in multivariate data analysis and semi-empirical modeling. In PLS and PCA the abnormal samples of data can be detected and analyzed by looking at scores and residuals. Outlier detection in OPLS presents no additional problem because the same principles apply.

The first steps in OPLS are to estimate the loadings w and p. OPLS calculates w and p with the generalized regression method projections to latent structures partial least squares (PLS). The number of orthogonal and non-orthogonal components used should be selected according to some significance criteria. The well known crossvalidation technique can be used. It is important to use some significance criteria when determining the number of PLS components. Underfitting or overfitting of data is serious to any empirical modeling, and consequently also for OPLS.

Scaling methods such as unit variance (UV) scaling where each column is divided with the standard deviation of that column, or pareto scaling where the weight factor is the square root of the standard deviation for that column is recommended. It is important to realize that the orthogonal variation in X removed from calibration samples, are assumed to exist in future samples as well. This assumption stems from the fact that the updating parameters W*_ortho, and P_ortho are estimated from the calibration data only. No variation only present in future samples, or only in calibration samples should be removed, this stresses the importance to only remove systematically relevant orthogonal components from the data. Removing that systematic irrelevant variation, and then applying scaling on the OPLS treated data can improve predictions.

The suggested OPLS method is truly versatile and if properly used, OPLS will improve data modeling, and interpretation regardless of most types of data properties. Suppose that a data set only contains relevant variation, consequently the OPLS method will not find any orthogonal components, and the resulting PLS model converges to a regular one component PLS solution. This is the case for data from designed experiments, where columns are orthogonal with respect to each other, and no orthogonal latent variables are present Also consider the opposite case, the data set only consisting of non-relevant information, here the OPLS method only finds orthogonal irrelevant variation, and no PLS component and therefore converges to a PCA solution.

OPLS can be designed to remove specific information. Instead of removing all systematic non-relevant variation in X, OPLS can be designed to remove specific types of variation in the X data. This is done by setting the unwanted property to y or Y. One example being the common problem of temperature differences for samples in NIR spectra that produce unwanted variation in the spectra. This provides the opportunity to analyze the specific systematic variation in X produced from temperature differences and also further analyze the OPLS treated data Xortho with minor influence of the disturbing variation that has been safely removed.

The OPLS method use the provided X and y or Y data to filter and remove variation in X not relevant to Y. If the given Y data include a great deal of noise, then there has been a concern that OPLS might not perform as well as it should, although the information removed from X indeed always is orthogonal to Y. Results from initial studies do not show any degradation of results compared to non-treated data. The use of crossvalidation, and/or eigenvalue criteria guides OPLS to perform well on most different types of data.

Perhaps the greatest advantage with the OPLS method is the improved interpretation of the data. Imagine a twelve component PLS model raising the questions:

What are the interesting variables for prediction of the response variable Y?

Which plots and parameters are interesting?

Some would analyze the regression coefficient vector, because that is used to predict Y from X. Others would say a combination of all loadings, scores, and the coefficient vector together with a look at the residuals. That sounds rather tough, but together with prior knowledge of the data that usually works. The OPLS method would make interpretation easier. First of all, it separates the relevant information from the non-relevant orthogonal information. Second of all, it gives an opportunity to analyze the non-relevant information in the data, and understand what the sources are for that. Third of all, the number of PLS components becomes much smaller, usually one or two components. Interpreting and analyzing the OPLS model clearly becomes much easier, and an interesting fact is that the first OPLS w loading is equivalent to the first PLS w loading of the original PLS model. That is easy to understand, but this raises an interesting point of the quality of the interpretation of PLS models.

Principal component analysis (PCA), the workhorse in multivariate data analysis. Only a brief description will be given here, more information can be found in H. Martens, T. Naes, Multivariate Calibration, Wiley, N.Y., 1989. Any data matrix X of size N*K, where N denotes the number of objects (rows), and K the number of variables (columns) can be decomposed into a number of principal components with PCA, as follows:

$$X=TP'+E$$

PCA evaluates the underlying dimensionality (latent variables) of the data, and gives an overview of the dominant patterns and major trends in the data.

Partial least squares (PLS), is a projection method that models the relationship between the response Y and the predictors X, see H. Martens et al. Blocks are decomposed as follows:

$$X=TP'+E,$$

$$Y=UC'+F.$$

Here T and U are the score matrices and P and C are the loading matrices for X and Y respectively, E and F are the residual matrices. The x-scores $t_a$ are linear combinations of the X-residuals or X itself where w is the weight vector, as follows:

$$t_a=(X-T_{a-1}*P_{a-1})*w_a.$$

This is provided in a way to maximize the covariance between T and U. W* are the weights that combine the original X variables (not their residuals as with w) to form the scores t, as follows:

$$W^*=W^*(P'^*W)^{-1}.$$

U is related to T by the inner relation:

$$U=T+H \text{ and } H=\text{Residual matrix}.$$

The predictive formulation for Y is as follows:

$$Y=TC'+F^*, \text{ where } F^* \text{ is the residual matrix}.$$

The following statistics for the regression models have been calculated.

Explained variance of X of the training set is as follows:

$$R2(X)=1-\Sigma(\hat{X}-X)^2/\Sigma X^2.$$

Explained variance of y of the training set is as follows:

$$R2(y)=1-\Sigma(\hat{y}-y)^2/\Sigma y^2$$

The predicted crossvalidated variance of Y of the training set is as follows:

$$Q2(y)=1-\Sigma(\hat{y}_{pred}-y)^2/\Sigma y^2.$$

Root mean square error of prediction of the test set is as follows:

$$RMSEP=\sqrt{\frac{\sum(\hat{y}-y)^2}{N}},$$

Distance to Model in X space, DmodX. Normalized residual standard deviation in X space, as follows:

$$DModX(i)=\frac{\sqrt{\frac{\Sigma(E_{ik})^2}{(K-A)}}}{s_0},$$

$$s_0=\sqrt{\frac{\Sigma\Sigma E_{ik}}{(N-A-A_0)*(K-A)}},$$

where K=the number of X variables, A=the number of PLS components, $A_0$=1 for column centered data. E=the residual matrix and N=number of objects in X.

NIR-VIS spectra were collected from the wavelength region 400–2500 nm. A NIR-Systems 6500 spectrometer was installed on top of a conveyer belt, and 151 baskets filled with different wood chips compositions were measured next to the conveyer belt at ASSI Domän pulp plant in Piteå, Sweden. The dry content was measured using a reference method. The wood chips dry content varied from 39–58%. From the data set N*K, where N=151 samples, and K=1050 digitized wavelengths, 51 spectra were randomly removed as a test set, leaving 101 spectra used as a training set for calibration. The number of PLS components were calculated according to crossvalidation.

Figure 2A:
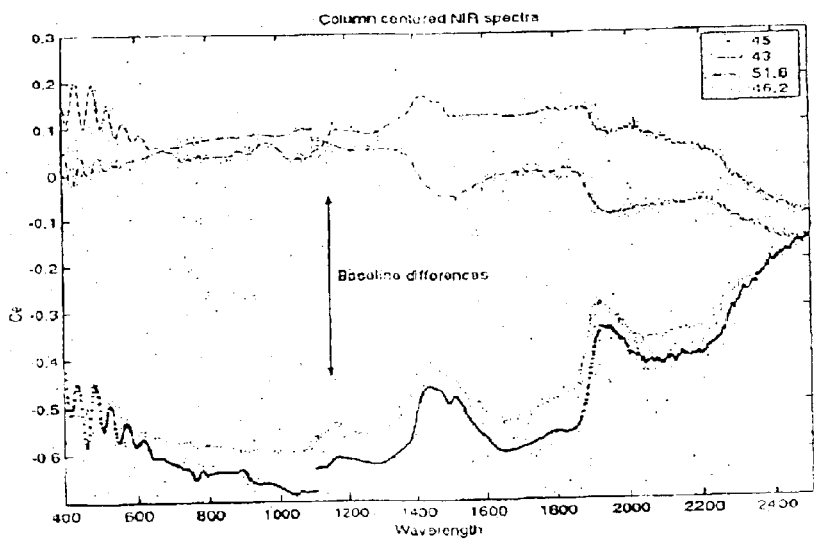
FIGS. 2a and 2b illustrate a figure example of the effect of OPLS, where an upper
Figure 2B:
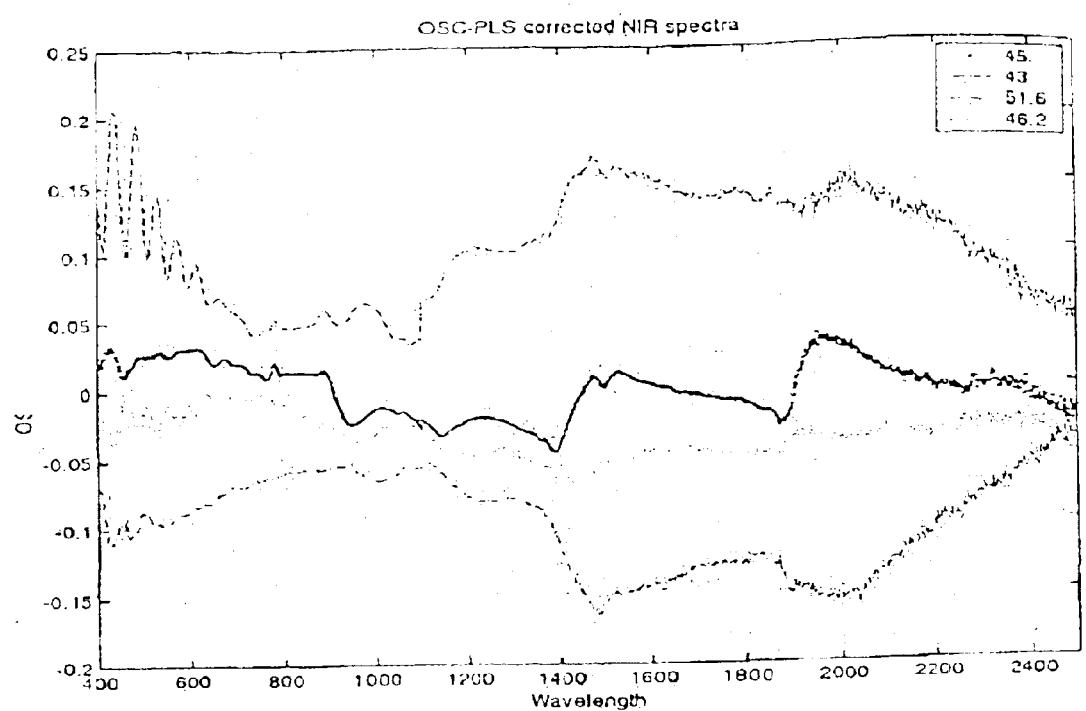

FIG. 2a illustrates column centered untreated NIR spectra and FIG. 2b OPLS treated NIR spectra in accordance with the present invention.

In FIGS. 2a and 2b, a comparison of NTR spectra before and after OPLS treatment is provided. The untreated NIR spectra displays a clear baseline variation with little relevance for moisture content Y, shown in the upper right corner of FIG. 2a. Irrelevant variation, baseline and slope problems, have been reduced as depicted in FIG. 2b. A difference in moisture content among samples produce most of the variation, and the baseline and slope problems earlier noted have been greatly reduced.

The result in Table 1 shows a clear reduction in the number of PLS components needed when OPLS was used.

TABLE 1

Data set: ASSI NIR (Number of comp. according to crossvalidation)

| Method | # Orthogonal comp. | # PLS comp. | R2Y | Q2Y | RMSEP |
|---|---|---|---|---|---|
| PLS | — | 5 | 0.80 | 0.73 | 2.95 |
| MSC + PLS | — | 2 | 0.80 | 0.81 | 3.13 |
| SNV + PLS | — | 3 | 0.81 | 0.81 | 3.09 |
| DO + PLS | 3 (not orthogonal) | 2 | 0.72 | 0.68 | 3.06 |
| OSC + PLS | 1 | 1 | 0.81 | 0.80 | 3.01 |
| OPLS | 4 | 1 | 0.80 | 0.78 | 2.95 |
| OPLS (PCA) | 1 | 1 | 0.80 | 0.78 | 2.94 |

The OSC method could only extract one component which was somewhat overfitted. Using a second OSC component resulted in a more serious overfit of the PLS model. It should be noted that the SNV, DO, and MSC methods did not perform well. They actually increased the prediction error, and worsened the results compared to the original PLS model. Neither of those methods guarantee orthogonality as to what is being removed from X, and therefore relevant information is sometimes lost. It should be pointed out that the DO method did not remove variation orthogonal to Y, and therefore also produced higher prediction errors than the original PLS model. Note that if PCA is used on $X_{ortho}$ to find the latent orthogonal components, and instead those are removed from X and not the whole $X_{ortho}$ matrix and scaling is applied, a clear decrease in the total number of components resulted. This shows that scaling after OPLS could improve modeling.

Figure 3:
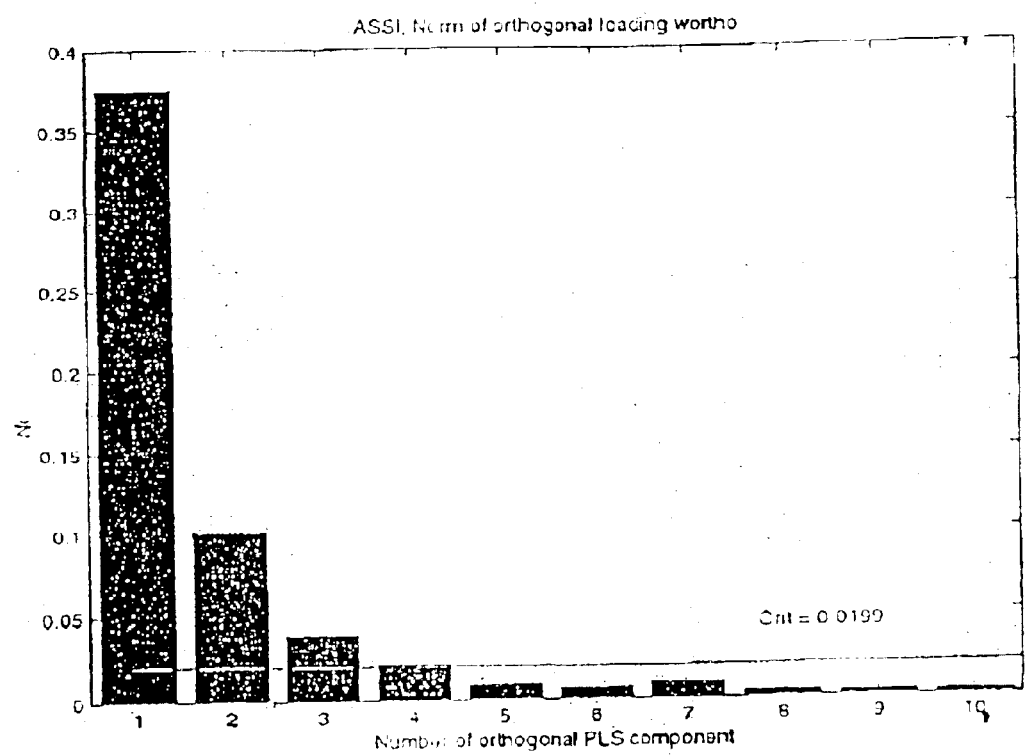
FIG. 3 illustrates the norm of an orthogonal vector.
Figure 4:
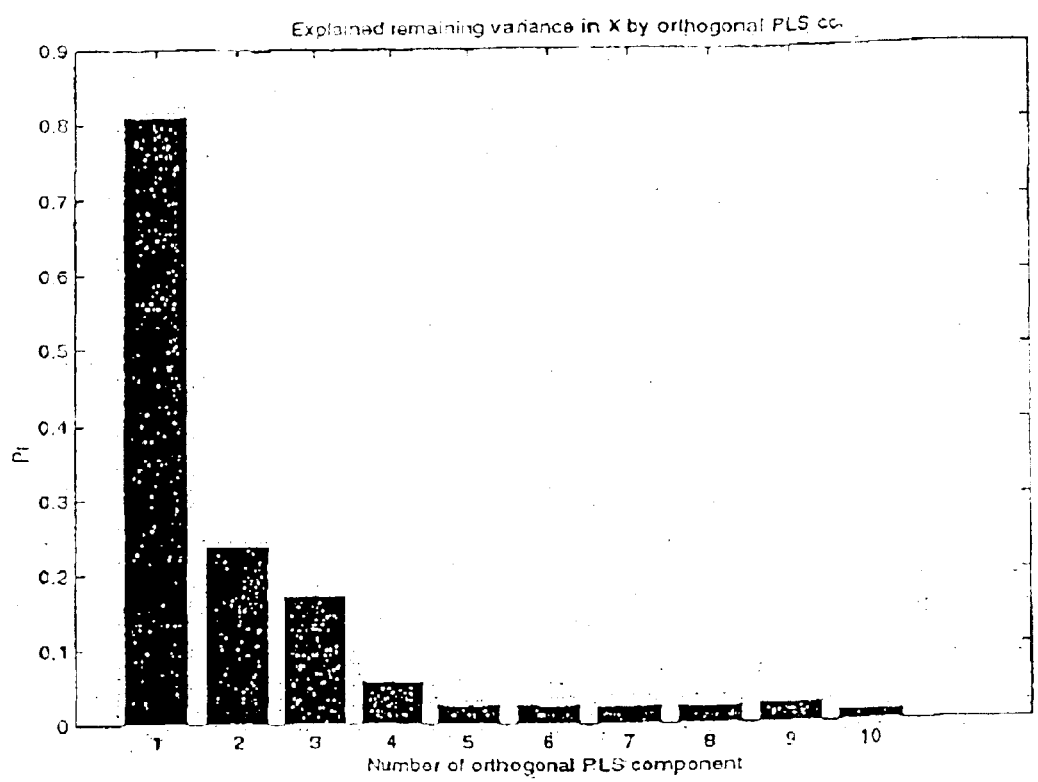
FIG. 4 illustrates an explained variation for orthogonal PLS components.

Determining a correct number of OPLS components should be made according to a significance criteria. The regular crossvalidation procedure can not be used here because the Y weight vector c becomes zero for all OPLS components. We suggest looking at the amount of orthogonal variation removed for each component, and also the norm of the $w_{ortho}$ vector found in step 8 in the OPLS method. If the norm is small compared to the norm of loading p, then little orthogonal variation in X was found in that component and the number of orthogonal PLS components have been found. An approach could be not to stop, but instead extract such components as regular PLS components, and continue the method until all variance in X has been accounted for. This allows the OPLS method to continue searching for orthogonal components hidden underneath the first ones. In FIG. 3, the normalized norm of the $w_{ortho}$ vector is shown. A clear trend is visible, and four orthogonal components were removed. Whether or not the fourth orthogonal component is relevant or not is difficult to say, as was the case for the original PLS model where the fifth PLS component was lose to being irrelevant. In FIG. 4, the explained variation for each orthogonal PLS component is plotted, and there is a clear similarity to FIG. 3. As a rule of thumb, the total number components for OPLS should never exceed the number of PLS components for the original PLS model.

FIG. 3. illustrates the norm of an orthogonal vector $w_{ortho}$, and FIG. 4 illustrates an explained variation for each orthogonal PLS component.

It is a great advantage with OPLS to be able to analyze the non-relevant information in X as orthogonal principal components. It should be clear that all information in those plots, scores and loadings are systematically non-relevant, orthogonal, to the wanted quality variable Y.

Figure 5:
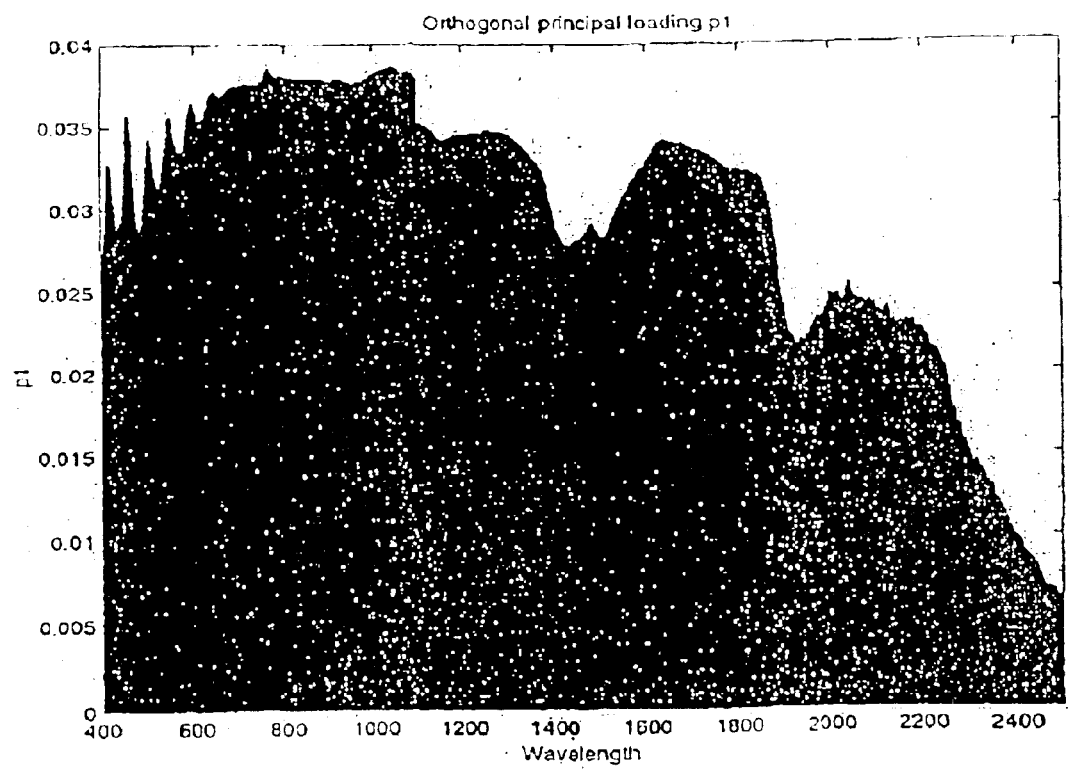
FIG. 5 illustrates a first principal orthogonal loading of a disturbing variation in X.
Figure 6:
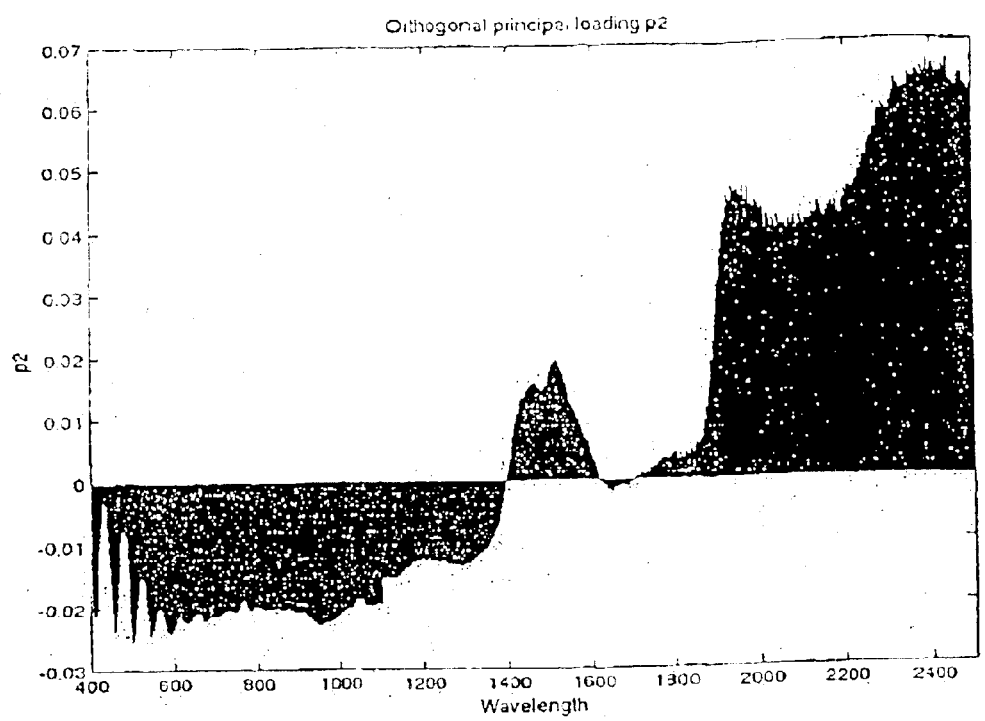
FIG. 6 illustrates a second principal orthogonal loading of a disturbing variation in X.

The first two orthogonal loadings are plotted in FIGS. 5 and 6. FIG. 5 illustrates a first principal orthogonal loading disturbing variation in X, and FIG. 6a second principal orthogonal loading of disturbing variation in X.

Figure 7:
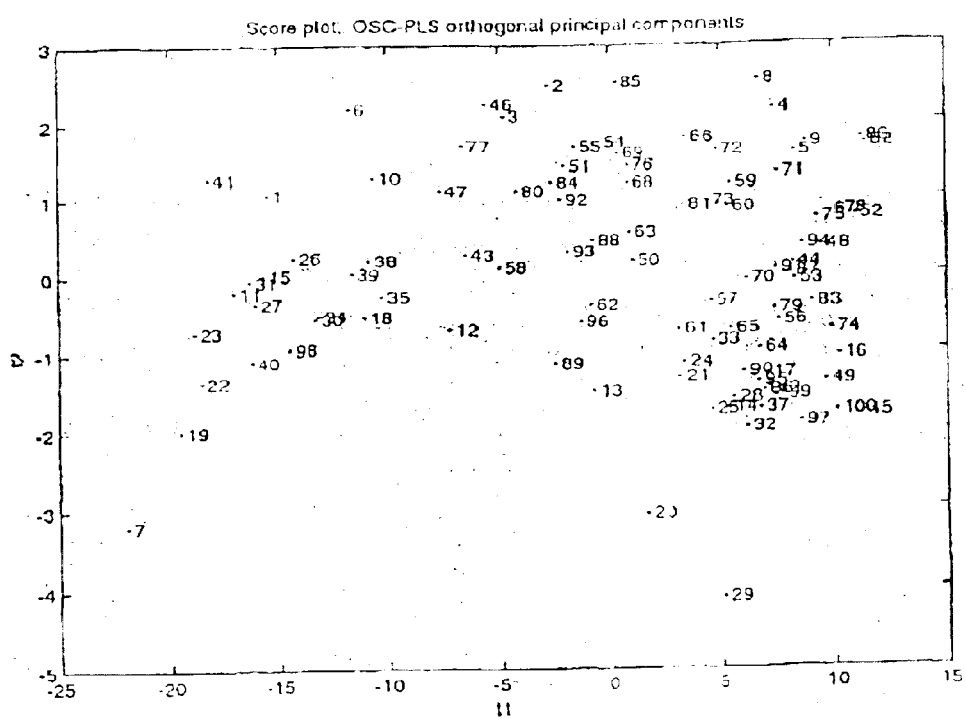
FIG. 7 illustrates a score plot t1-t2 of orthogonal principal components.

It can clearly be seen that the orthogonal components are in fact basically an offset shift and a slope difference. Those irrelevant variations were detected and removed with OPLS. The question may be asked; How come the multiplicative scatter correction (MSC) method, designed to remove these types of disturbances from NIR spectra, did not manage to produce better results? One simple reason could be that the MSC target vector (usually column mean vector) used to correct all other spectra is not a good choice. The OPLS method finds those correction vectors from the data, and also guarantees that the information removed is not relevant for the modeling of Y. The corresponding score plot for the orthogonal latent components is shown in FIG. 7, which illustrates a score plot t1-t2 of orthogonal principal components.

Figure 8:
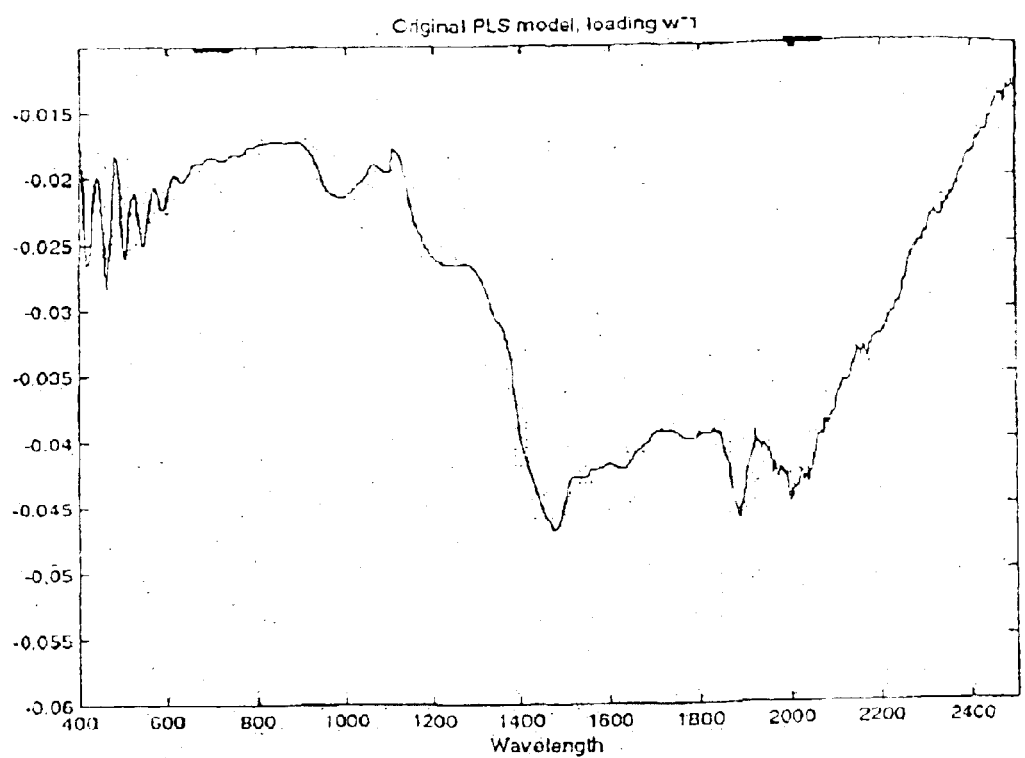
FIG. 8 illustrates a first loading w1 from an original PLS model.
Figure 9:
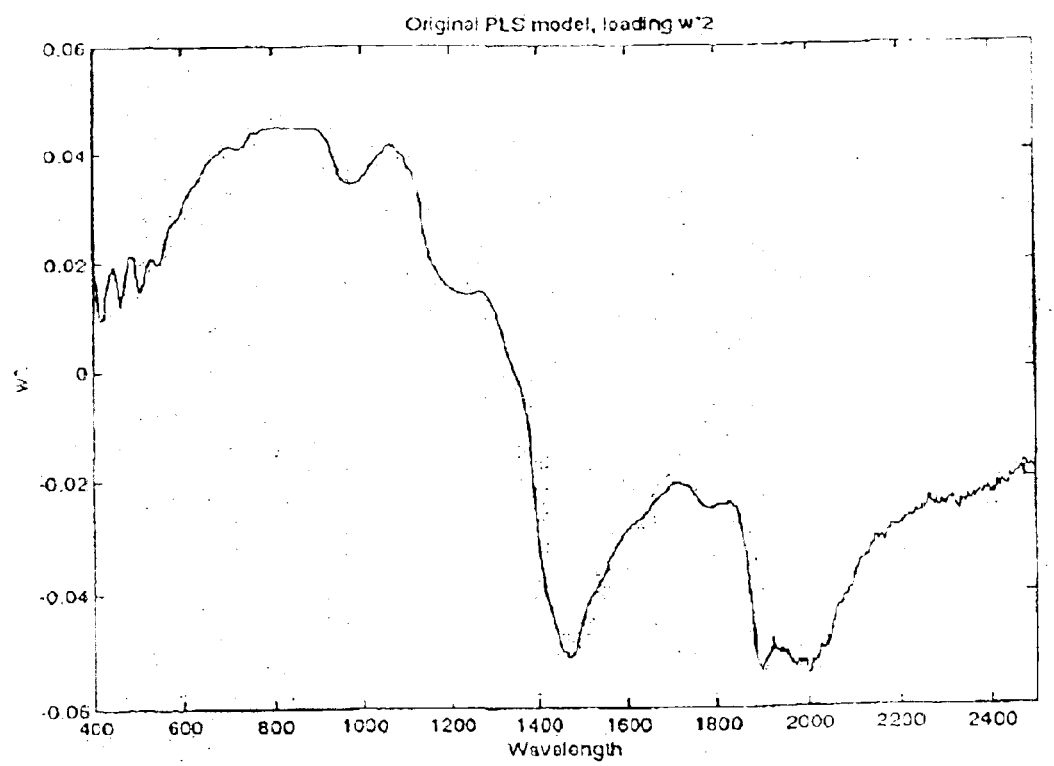
FIG. 9 illustrates a second loading w2 from original PLS model.

OPLS gives the possibility to analyze the irrelevant variation in data in orthogonal components (scores and loadings). All variation in the score plots are of no relevance for Y, and therefore the source of unwanted variation can perhaps be found and removed, or reduced. In industrial processes it is not always possible to remove unwanted variation, but OPLS offers the advantage to at least know what type of disturbing variation that exists, and possibly find methods to reduce it. Is it possible to know in advance where applying OPLS will help? In principle, all PLS models with more than one PLS component should benefit from using OPLS. Consider designed data with orthogonal variables. Only one PLS component is needed because no latent orthogonal variation is present. In FIGS. 8 and 9, a good example of when to use OPLS is displayed and this phenomenon often occurs for NIR spectra. The first two w loadings from the original PLS model are plotted.

FIG. 8 illustrates a first loading w1 from an original PLS model, and FIG. 9 illustrates a second loading w2 from an original PLS model.

The reason why the first two loadings are similar is that the X data matrix contains large baseline variations (non-relevant) orthogonal to Y. This causes problems for the PLS method. PLS is forced to include some X-Y covariance in each PLS component, even though the a great deal of the X variation is orthogonal to Y. PLS solves this by peeling of information from the X matrix in a couple of components, leading to a more complex PLS model harder to interpret.

Table 2 shows the PLS model parameters for the original PLS model, and also the OPLS treated PLS model.

TABLE 2

| Original PLS model | | | | OPLS PLS model | | | |
|---|---|---|---|---|---|---|---|
| PLS Comp | R2Xcum | R2Ycum | Q2cum | PLS Comp | R2Xcum | R2Ycum | Q2cum |
| 1 | 0.948 | 0.107 | 0.093 | 1 | 0.976 | 0.796 | 0.782 |
| 2 | 0.987 | 0.499 | 0.478 | | | | |
| 3 | 0.995 | 0.629 | 0.587 | | | | |
| 4 | 0.996 | 0.757 | 0.695 | | | | |
| 5 | 0.997 | 0.796 | 0.731 | | | | |

A clear sign when to use the OPLS preprocessing method is given in Table 2. The amount of variance R2Ycum, (or crossvalidated Q2cum) is relatively small in the first component. The amount of explained variation in X, R2Xcum is rather large. This is a clear indication that large orthogonal variation with regards to Y exists in X, and where OPLS could improve modeling and interpretation. In this case, the orthogonal components revealed that baseline variations were the cause of the large unwanted variation in X. For other types of data, the orthogonal components could appear later in the PLS components, but here the baseline problems introduced such large variation in data, and it appeared in the first component. The OPLS model required only one PLS component because all relevant orthogonal latent variation had already been removed. Once again consider designed experiments where the data have orthogonal variables. These models only require one PLS component, and the reason is easy to understand. The designed data do not contain any orthogonal latent variation, and therefore the PLS model only needs one component.

The number of PLS components for the OPLS pretreated PLS model are greatly reduced, making interpretation easier compared to the original PLS model. The scores are not masked anymore with irrelevant variation, which has been greatly suppressed with OPLS.

Figure 10:
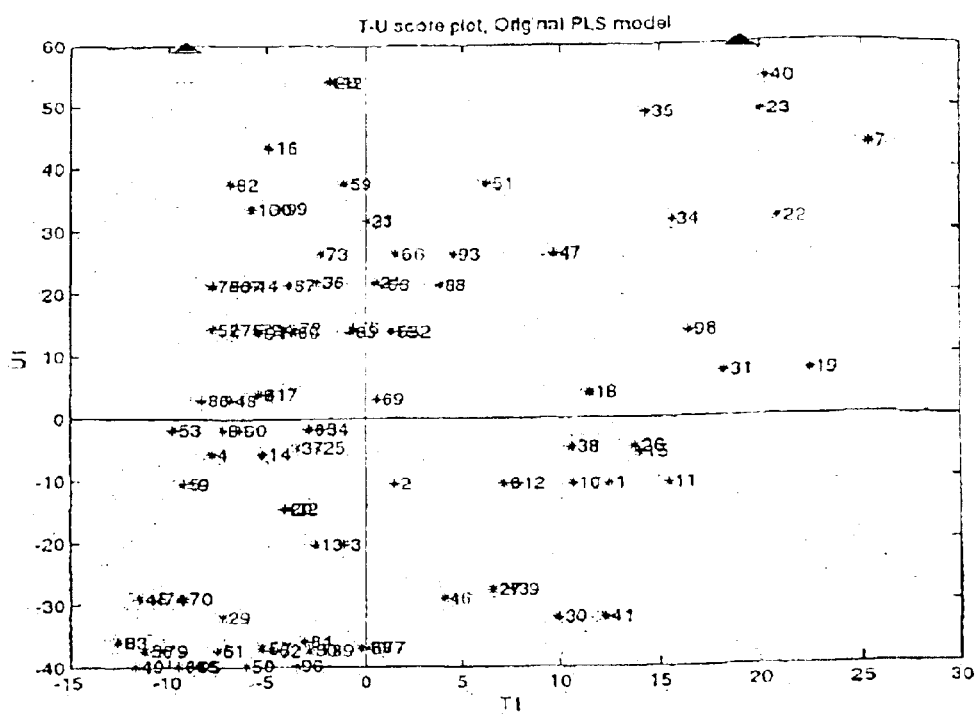
FIG. 10 illustrates a t1-u1 score plot of an original PLS model.
Figure 11:
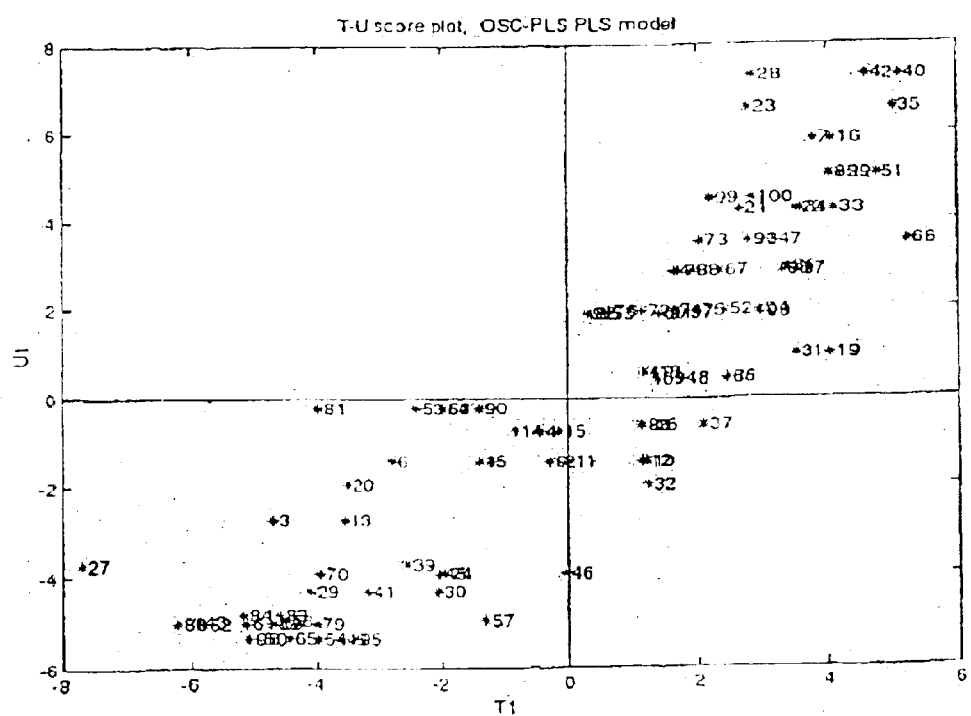
FIG. 11 illustrates t1-u1 score plot of OPLS pretreated PLS model according to the present invention.

FIG. 10 illustrates a t1-u1 score plot of an original PLS model and FIG. 11 illustrates a t1-u1 score plot of an OPLS pretreated PLS model according to the present invention.

The t-u correlation in the OPLS treated PLS model is much more distinct and clear. The original PLS model FIG. 10 do not show much correlation in the first PLS component, and the reason is mainly due to the disturbing baseline variation. In FIG. 11 the baseline variations, and slope differences have been removed, and the PLS model only needs one component to model the X-Y relationship.

Figure 12:
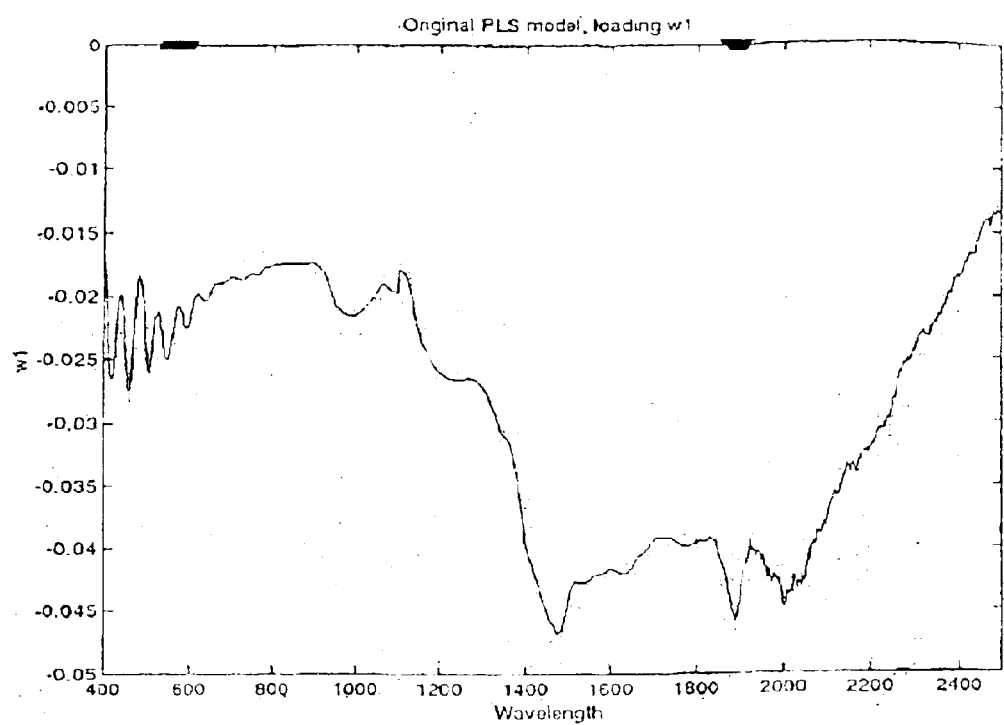
FIG. 12 illustrates a first loading w1 from an original PLS model.
Figure 13:
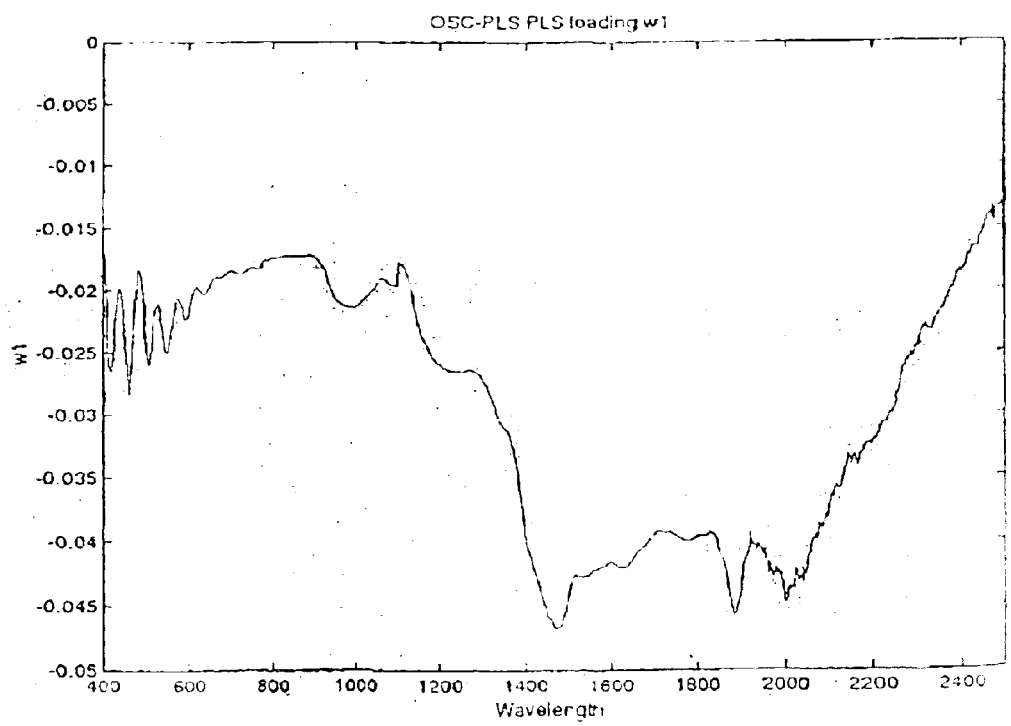
FIG. 13 illustrates a first loading w1 from an OPLS pretreated PLS model according to the present invention.

In FIGS. 12 and 13, the first loading vector w is plotted for the original PLS model, and the OPLS pretreated PLS model. Notice that the first loading w in the original PLS model is identical to the first loading w in the OPLS pretreated PLS model. This is easily understood when realizing that w is the projection of the matrix X onto the vector u, y if only one column in Y, using the NIPALS method. Removing orthogonal components from X do not disturb the correlation between X and Y because orthogonal columns in X do not influence the projection w=u'X/(u'u).

FIG. 12 illustrates a first loading w1 from an original PLS model, and FIG. 13 illustrates a first loading w1 from an OPLS pretreated PLS model.

This brings us to the interesting subject of interpretation. Both the original PLS model, and OPLS pretreated PLS model have the same first loading weight vector w, but different scores are produced. This means that the PLS weight vector w is not very useful when orthogonal variation is present. The loading vector p is more relevant to analyze with respect to the scores. However, the loadings p are influenced by both the relevant and the irrelevant variation in X mixed together This makes the interpretation of the PLS model difficult. Physico-chemical interpretation of the scores with regards to what variables are important for prediction and what variables produce disturbing variation in X. OPLS splits the two separate variations in data into two different data matrices that are analyzed individually and independently of each other.

It is clear that the regression coefficients of the original PLS model and the OPLS pretreated PLS model must be very different. See FIGS. 14 and 15.

The difference originates from the amount of orthogonal information in X that is present in the original PLS model. The regression coefficients display the variables using the current data that are important for the modeling of Y. Removing as much of the irrelevant variation in X is important to gain relevant and maximum knowledge of the system under investigation, and to keep the model complexity to a minimum. Additionally, analyzing the orthogonal variation in terms of orthogonal principal components (scores and loading) to find and reduce the irrelevant variation in data could sometimes be crucial. The suggested OPLS method is a good method to employ for that purpose.

The present invention OPLS method has been shown to be generic and versatile. It can be made an integrated part of the regular PLS modeling, improving interpretation and model predictions, or it can be used as a preprocessing method for removing disturbing variation from data. In example given, the disturbing variation was effectively removed and analyzed with the help of principal component analysis (PCA), also the resulting one component PLS model was easier to interpret. The OPLS method can be seen as a filtering method, where variation irrelevant for the problem at hand is effectively removed. This applies not only for calibration purposes, but for all types of filtering where irrelevant variation in the data X is to be reduced or removed. For example, industrial process signals have drift, and other disturbing variations. Applying OPLS with time as Y would reveal variation in X related to time drift. Another example is in Quantiative Structure Activity Relationships (QSAR) modeling. Interpretation of their models is vital, and OPLS offers the possibility to separate the relevant variation in data from the non-relevant variation. Internal validation methods such as crossvalidation and eigenvalue criteria ensures that the OPLS method will work on most types of data. Compared to the earlier proposed OSC method, no time consuming iteration is present in the method. Because OPLS is based on the PLS-NIPALS method, it works with moderate amounts of missing data. The most clear advantage of using the OPLS method is the improvement in interpretation of PLS models and their parameters scores, loadings, and residuals.

It is thus believed that the operation and construction of the present invention will be apparent from the foregoing description. While the method and arrangement shown or described has been preferred it will be obvious that various changes and modifications may be made therein without departing from the spirit and scope of the invention as defined in the attached claims.

What is claimed is:

1. A method for concentration or property calibration of input data from samples of substances or matter, said calibration determining a filter model for further samples of the same substance or matter comprising to optionally transform, center, and scale the input data to provide a descriptor set (X) and a concentration or property set (y, Y), characterized in that the method removes information or systematic variation in the input data that is not correlated to the concentration or property set by providing the steps of:

producing a descriptor weight set (w), which is normalized, by projecting the descriptor set (X) on the concentration or property set (y, Y), projecting the descriptor set (X) on the descriptor weight set (w) producing a descriptor score set (t), projecting the descriptor set (X) on the descriptor score set (t), producing a descriptor loading set (p), projecting the property set (y) on the descriptor score set (t), producing a property weight set (c), projecting the property set (y) on the property weight set (c), producing a property score set (u);

comparing the descriptor loading set (p) and the descriptor weight set (w), and their difference (p−w), thus obtaining the part of the descriptor loading set (p) that is unrelated to the property set (y);

using said difference weight set (wortho), normalized, as a starting set for partial least squares analysis;

calculating the corresponding orthogonal descriptor score set (tortho) as the projection between the descriptor set (X) and said normalized orthogonal difference weight set (wortho), and calculating a corresponding orthogonal descriptor loading set (portho) as the projection of the descriptor set (X) onto the orthogonal descriptor score set (tortho);

removing the outer product of the orthogonal descriptor score set (tortho) and the orthogonal descriptor loading set (portho') from the descriptor set (X), thus providing residuals data (E), which is provided as the descriptor set (X) in a next latent variable component;

repeating the above steps for each orthogonal latent variable component;

filtering from the residuals data (E) strong systematic variation that can be bilinearly modeled as the outer product of the orthogonal descriptor score set and the orthogonal orthogonal descriptor loading set (portho') from the descriptor set (X), thus providing residuals data (E), which is provided as the descriptor set (X) in a next latent variable component;

repeating the above steps for each orthogonal latent variable component;

filtering from the residuals data (E) strong systematic variation that can be bilinearly modeled as the outer product of the orthogonal descriptor score set and the orthogonal descriptor loading set (Torth*Portho'), thus providing an orthogonal descriptor set (Xortho) being orthogonal to the property set (y, Y);

optionally providing a principal component analysis (PCA) on the orthogonal descriptor set (Xortho), producing a bilinear decomposition of the orthogonal descriptor set (Xortho) as the outer product of the principal component analysis score set and the principal component analysis loading set and principal component analysis residuals (Tpcaortho*Ppcaortho'+ Epcaortho), adding the principal component analysis residuals data (Epcaortho) back into filtered residuals data (E);

filtering new data with the following steps:

projecting a new descriptor set (xnew') onto the normalized orthogonal difference weight set (wortho), thus producing a new orthogonal descriptor score set (tnewortho) and removing the product between the new orthogonal descriptor score set (tnewortho) and the orthogonal descriptor loading set (portho') from the new descriptor set (xnew'), thus providing new residuals (enew'), which are provided as a new descriptor set (xnew') in a next orthogonal component;

repeating said two filtering steps for new data for all estimated orthogonal components;

computing a new orthogonal descriptor set (xnewortho'= tnewortho*Portho') as the outer product of the new orthogonal descriptor score set (tnewortho) and the orthogonal descriptor loading set (portho'), computing a new orthogonal principal component score set (tnewpcaortho) from the projection of the new orthogonal descriptor set onto the principal component analysis loading set (xnewortho'*Ppcaortho'), whereby the new principal component analysis residuals formed (enewpcaortho=xnewortho'−tnewpcaortho* Ppcaortho') are added back into the new residuals (enew') if principal component analysis was used on the orthogonal descriptor set (Xortho), and only the outer product of the principal component analysis score sets and the principal components loading set (Tpcaortho*Ppcaortho') was removed from the original descriptor set (X); and for multiple concentration or property sets (Y), calculating a principal component analysis model on said property sets (Y=TP'+E) and repeating the above steps for each separate principal component analysis score set (t) and use the orthogonal descriptor ($X_{ortho}$) as the input descriptor set (X) for each subsequent principal component analysis score set (t), thus making up said filtering model for filtering of further samples of the same type.

2. A method according to claim 1, characterized in that:

performing an ordinary PLS analysis with the filtered residuals data (E) and the concentration or property set (y, Y);

performing an ordinary PLS analysis with said filtered new residuals set (enew') as prediction set.

3. A method according to claim 2, characterized in that by finding said orthogonal components for each component seperately an amount of disturbing variation in each partial least square component can be analyzed.

4. A method according to claim 2, characterized in that the method uses crossvalidation and/or eigenvalue criteria for reducing overfitting.

5. A method according to claim 2, characterized in that said principal component analysis (PCA) components are chosen acordidng to a crossvalidation or eigenvalue criteria.

6. A method according to claim 2, characterized in that the method includes a step to remove specific types of variation in the descriptor set (X), when an unwanted or non-relevant concentration or property set (y) or (Y) exist by using the orthogonal descriptor ($X_{ortho}$) as a data set of interest, as it contains no correlated variation to the concentration or property set (y, Y).

7. A method according to claim 1, characterized in that by finding said orthogonal components for each component separately an amount of disturbing variation in each partial least square component can be analyzed.

8. A method according to claim 1, characterized in that the method uses crossvalidation and/or eigenvalue criteria for reducing overfitting.

9. A method according to claim 1, characterized in that said principal component analysis (PCA) components are chosen according to a crossvalidation or eigenvalue criteria.

10. A method according to claim 1, characterized in that the method includes a step to remove specific types of variation in the descriptor set (X), when an unwanted or non-relevant concentration or property set (y) or (Y) exist by using the orthogonal descriptor ($X_{ortho}$) as a data set of interest, as it contains no correlated variation to the concentration or property set (y, Y).

11. An arrangement for concentration or property calibration of input data from samples of substances or matter, said calibration determining a filter model for further samples of the same substance or matter comprising to optionally transform, center, and scale the input data to provide a descriptor set (X) and a concentration or property set (y, Y), characterized in that said filter model removes information or systematic variation in the input data that is not correlated to the concentration or property set, comprising:

projecting means for producing a descriptor weight set (w), which is normalized, by projecting the descriptor set (X) on the concentration or property set (y, Y);

projecting means for the descriptor set (X) on the descriptor weight set (w) producing a descriptor score set (t);

projecting for the descriptor set (X) on the descriptor score set (t) producing a descriptor loading set (p);

projecting means for the property set (y) on the descriptor score set (t) producing a property weight set (c);

projecting means for the property set (y) on the property weight set (c) producing a property score set (u);

comparing means for the descriptor loading set (p) and the descriptor weight set (w), and their difference (p−w), thus obtaining the part of the descriptor loading set (p) that is unrelated to the property set (y, Y);

using said difference weight set (wortho), normalized, as a starting set for partial least squares analysis;

first calculating means for the corresponding orthogonal descriptor score set (tortho) as the projection between the descriptor set (X) and said normalized orthogonal difference weight set (wortho), and for calculating a corresponding orthogonal descriptor loading set (portho) as the projection of the descriptor set (X) onto the orthogonal descriptor score set (tortho);

second calculating means for removing the outer product of the orthogonal descriptor score set (tortho) and the orthogonal descriptor loading set (portho') from the descriptor set (X), thus pr residuals data (E), which is provided as the descriptor set (X) in a next component;

the above means being repeatedly used for each orthogonal latent variable component;

first filtering means for the residuals data (E) from strong systematic variation that can be bilinearly modeled as the outer product of the orthogonal descriptor score set and the orthogonal descriptor loading set (Tortho*Portho'), thus providing an orthogonal descriptor set (Xortho) being orthogonal to the property set (y, Y);

optionally providing analyzing means for a principal component analysis (PCA) on the orthogonal descriptor set (Xortho), producing a bilinear decomposition of the orthogonal descriptor set (Xortho) as the outer product of the principal component analysis score set and the principal component analysis loading set and principal component analysis residuals (Tpcaortho*Ppcaortho'+Epcaortho), adding the principal component analysis residuals data (Epcaortho) back into filtered residuals data (E);

second filtering means for new data including:
projecting means for a new descriptor set (xnew') onto the normalized orthogonal difference weight set (wortho), thus producing a new orthogonal descriptor score set (tnewortho); and calculating means for removing the product between the new orthogonal descriptor score set (tnewortho) and the orthogonal descriptor loading set (portho') from the new descriptor set (xnew'), thus providing new residuals (enew'), which are provided as a new descriptor set (xnew') in a next orthogonal component;

said second filtering means of new data being repeatedly for estimated orthogonal components;

calculating means for a new orthogonal descriptor set (xnewortho'=tnewortho*Portho') as the outer product of the new orthogonal descriptor score set (tnewortho) and the orthogonal descriptor loading set (portho'), calculating a new orthogonal principal component score set (tnewpcaortho) from the projection of the new orthogonal descriptor set onto the principal component analysis loading set (xnewortho'* Ppcaortho'), whereby the new principal component analysis residuals formed (enewpcaortho=xnewortho'−tnewpcaortho*Ppcaortho') are added back into the new residuals (enew') if principal component analysis was used on the orthogonal descriptor set (Xortho), and only removing the outer product of the principal component analysis score sets and the principal components loading set (Tpcaortho*Ppcaortho') was removed from the original descriptor set (X); and for multiple concentration or property sets (Y), means for calculating a principal component analysis model on said property sets (Y=TP'+E) and repeatedly using the above means for each separate principal component analysis score set (t) and using the orthogonal descriptor ($X_{ortho}$) as the input descriptor set (X) for each subsequent principal component analysis score set (t), thus making up said filtering model for filtering of further samples of the same type.

12. An arrangement according to claim 11, characterized in that:
partial least square analysis means for the filtered residuals data (E) and the concentration or property set (y, Y), and for said filtered new residuals set (enew') as prediction set.

13. An arrangement according to claim 12, characterized in that by finding said orthogonal components for each component separately an amount of disturbing variation in each partial least square component can be analyzed by said analyzing means.

14. An arrangement according to claim 12, characterized in that the arrangement uses crossvalidation and/or eigenvalue criteria for reducing overfitting.

15. An arrangement according to claim 12, characterized in that said principal component analysis (PCA) components are chosen according to an crosssvalidation or eigenvalue criteria by said analyzing means.

16. An arrangement according to claim 12, characterized in that the arrangement removes specific types of variation in the descriptor set (X), when an unwanted or non-relevant concentration or property set (y) exist by using the orthogonal descriptor ($X_{ortho}$) as a data set of interest, as it contains no correlated variation to the concentration or property set (y,Y).

17. An arrangement according to claim 11, characterized in that by finding said orthogonal components for each component separately an amount of disturbing variation in each partial least square component can be analyzed by said analyzing means.

18. An arrangement according to claim 11, characterized in that the arrangement uses crossvalidation and/or eigenvalue criteria for reducing overfitting.

19. An arrangement according to claim 11, characterized in that said principal component analysis (PCA) components are chosen according to an crossvalidation or eigenvalue criteria by said analyzing means.

20. An arrangement according to claim 11, characterized in that the arrangement removes specific types of variation in the descriptor set (X), when an unwanted or non-relevant concentration or property set (y) exist by using the orthogonal descriptor ($X_{ortho}$) as a data set of interest, as it contains no correlated variation to the concentration or property set (y, Y).

* * * * *

UNITED STATES PATENT AND TRADEMARK OFFICE
CERTIFICATE OF CORRECTION

PATENT NO. : 6,853,923 B2  Page 1 of 1
APPLICATION NO. : 10/204646
DATED : February 8, 2005
INVENTOR(S) : Johan Trygg and Svante Wold It is certified that error appears in the above-identified patent and that said Letters Patent is hereby corrected as shown below:

1) In column 5, line 4 ";" should be -- . --
2) In column 5, line 40 after "sets" -- the invention includes -- should be inserted.
3) In column 8, line 34 "multivatiate" should be -- multivariate --
4) In column 9, line 16, in equation "$e_2 - {}_e1-t_2p_2'$" should be -- $e_2 = e_1-t_2p_2'$ --
5) In column 10, line 9, in chart #3 "/ /" should be -- / --
6) In column 11, line 25, -- [ -- should be inserted before "Wortho"
7) In column 11, line 41, "Pbs" should be -- PLS --
8) In column 11, line 49, after "first" -- t -- should be inserted
9) In column 13, line 66, "which" should be --wortho--
10) In column 14, line 40, after "steps" --are-- should be inserted
11) In column 15, line 6, "comprised" should be deleted
12) In column 15, line 48, "is optionally providing" should be --optionally includes --
13) In column 16, line 16, ";" should be -- . --
14) In column 17, line 20, "avid" should be --and--
15) In column 17, line 30, "ortho" should be --ortho'--
16) In column 19, line 6, after "present" -- . -- should be inserted. Also wrong in sub. spec.
17) In column 22, line 8, "lose" should be --close--
18) In column 24, line 17, after "together" -- . -- should be inserted.
19) In column 26, line 7, after "following" --two-- should be inserted
20) In column 26, line 62, "accordidng" should be --according--
21) In column 28, line 11, after "for" --filtering--should be inserted
22) In column 28, line 24, after "for" --all-- should be inserted Signed and Sealed this Thirtieth Day of October, 2007

JON W. DUDAS
*Director of the United States Patent and Trademark Office*